USOO5641863A

United States Patent [19]
Schreiber et al.

[11] Patent Number: 5,641,863
[45] Date of Patent: Jun. 24, 1997

[54] CHIMERIC IGG FC RECEPTORS

[75] Inventors: Alan D. Schreiber, Philadelphia; Jong-Gu Park, Drexel Hill, both of Pa.

[73] Assignee: University of Pennsylvania, Philadelphia, Pa.

[21] Appl. No.: 273,846

[22] Filed: Jul. 12, 1994

Related U.S. Application Data

[62] Division of Ser. No. 129,391, Sep. 30, 1993, abandoned.

[51] Int. Cl.$^6$ ........................ C07K 19/00; C07K 14/705
[52] U.S. Cl. ........................ 530/350; 435/69.7; 536/23.4
[58] Field of Search ........................ 435/69.7; 530/350; 536/23.4

[56] References Cited

PUBLICATIONS

Amigorena et al., *Nature* 358:337–341, 23 Jul. 1992.
Hibbs et al., *P.N.A.S.* 85:2240–2244, Apr. 1988.
Stuart et al, *J. Exp. Med.* 166:1668–1684, Dec. 1982.
Bonnerot et al., *EMBO J.* 11(7):2747–2758, Jul. 1982.
Yagi et al, "Cloning of the cDNA for the Deleted Syk Kinase Homologous to Zap–70 From Human Basophilic Leukemia Cell Line (KU812)", Biochemical and Biophysical Research Communications 200(1):28–34 (1994).
Mitchell et al, "Structural Requirements for Phagocytosis by the Fc Receptor FcγRIIA", 1993 Clinical Research 41(2):189A.
Park et al, "The Structure of the γ chain Fc Receptor Subunit Determines Phagocytic Function of Macrophage FcγRIII (FcγRIIIA)", 1993 Clinical Research 41(2):324A.
Mantaring et al, "The B–Cell Antigen Receptor Subunit Ig–α Mediates A Phagocytic Signal", 1993 Clinical Research 41(2):134A.
Rossman et al, "Alterations in Monocyte/Macrophage Fcγ Receptor Expression in the Acute Respiratory Distress Syndrome (ARDS)", 1993 Clinical Research 41(2):251A.
Indik et al, "The High Affinity Fcγ (CD64) Induces Phagocytosis in the Absence of its Cytoplasmic Domain", 1993 Clinical Research 41(2).
Indik et al, "Human FcγRII: The Structure of the FcγRII Cytosolic Domain Governs Phagocytic Function", 1992 Clinical Research 40(2):349A.
Indik et al, "The Structure of the FcγRII Cytosolic Domain Influences Phagocytosis", 1992 FASEB J. 6(5):1613 Abstract.
Mitchell et al, "Structural Requirements of the Human Fc Receptor FCγRIIA in Phagocytosis", 1993 AAI/CIS Abstract J. Immunol. 150(8) Part 2 306A.
Hunter et al, "FcγRIII Mediated Phagocytosis and Receptor Phosphorylation Does Not Require The Protein Tyrosine Kinase Src.", Clinical Research 41(2):244A.
Munn et al, "Role of Low–Affinity Fc Receptors in Antibody–dependent Tumor Cell Phagocytosis by Human Monocyte–derived Macrophages", Cancer Research 51:1117–1123 (1991).
Friedman, "Progress Toward Human Gene Therapy", Science 244:1275–1281 (1989).
Friedman et al, "Effect of Estradiol and Steroid Analogues on the Clearance of Immunoglobulin G–coated Erythrocytes", J. Clin. Invest. 75:162–167 (1985).
Indik et al, "Human FcγRII, in the Absence of Other Fcγ Receptors, Mediates a Phagocytic Signal", J. Clin. Invest. 88:1766–1771 (1991).
Rosenberg, Steven A., "Newer Approaches to Cancer Treatment", Cancer: Principles & Practice of Oncology, Fourth Edition, 2:2598–2613.
Amigorena et al, "Tyrosine–containing motif that transduces cell activation signals also determines internalization and antigen presnetation via type III receptors for IgG", Nature 358:337–341 (1992).
Cassel et al, "Differential Expression of FcγRIIA, FcγRIIB and FcγRIIC in Hematopoietic Cells" Analysis of Transcripts, Molecular Immunology 30(5):451–460 (1993).
Anderson, "Prospects for Human Gene Therapy", Science 226:401–409 (1984).
Pound et al, "Human FcγRI Triggering of the Mononuclear Phagocyte Respiratory Burst", Molecular Immunology 30(5):469–478 (1993).
Agarwal et al, "Involvement of $p72^{syk}$, a Protein–Tyrosine Kinase, in Fcγ Receptor", The Journal of Biological Chemistry 268(21):15900–15905 (1993).
Rossi and Sarver, "RNA enzymes (ribozymes) as antiviral therapeutic agents", TIBTECH 8:179–183 (1990).
Akerley III et al, "Neutrophil Activation Trhough High–Affinity Fcγ Receptor Using a Monomeric Antibody With Unique Properties", Blood 77(3):607–615 (1991).
Shohat et al, "Inhibition of cell growth mediated by plasmids encoding p53 anti–sense", Oncogene 1:277–283 (1987).
Indik et al, "Examination of Phagocytosis by Chimeric Fcγ Receptors", Journal of Immunology 150(8), Part II, issued Apr. 15, 1993, p. 306A, abstract No. 1754.
Ruiz et al, "Structural Features of the *In Vivo* Steroid Effect on Macrophage Fcγ Receptors", FASEB J. 4:A1758 (1990).
Indik et al, "Examination of Phagocytosis by Chimeric Fcγ Receptors", J. Immunol. 150:306A (1993).
Ruiz et al, "Macrophage Fcγ Receptor Expression: *In Vivo* Regulation by Human Recombinant Macrophage Colony Stimulating Factor (hrM–CSF)", Clin. Res. 40:796A (1992).
Ruiz et al, "Hormonal Regulation of Macrophage Fcγ Receptor Expression *In Vivo*", Clin. Res. 38:367A (1990).
Keller et al, "FcγRIIA is the Platelet Fc Receptor" Blood 211:55a (1992).

(List continued on next page.)

*Primary Examiner*—John Ulm
*Attorney, Agent, or Firm*—Nixon & Vanderhye P.C.

[57] ABSTRACT

The present invention relates, in general, to methods of stimulating phagocytosis and thereby combating infection and/or modulating immune complex disease, in particular, to methods of modulating the number and type of Fc receptors present on cells that normally possess such receptors, including monocytes and macrophages, as well as on cells that normally do not possess Fc receptors, such as fibroblasts, and to compounds and compositions suitable for use in such methods.

12 Claims, 12 Drawing Sheets

PUBLICATIONS

Huang et al, "Activation of the Platelet Fcγ Receptor by Anti–Platelet Antibodies", Blood 210:55a (1992).

Park et al, "Mapping the Structure of the Fc Receptor, FcγRIIIA, Required for Phagocytosis", Blood 996:251a (1992).

Darby et al, "Macrophage FcγRIII Signaling Induces Protein Tyrosine Kinase Activation", Blood 1398:352a (1992).

Mitchell et al, "Structure–Function Relationships of the Fcγ Receptor, FcγRIIA, In Transmission of a Phagocytic Signal", Blood 627:159a (1992).

Tuijnman et al, "Human Low–Affinity IgG Receptor FcγRIIa (CD32) Introduced Into Mouse Fibroblasts Mediates Phagocytosis of Sensitized Erythrocytes", Blood 79(7):1651–1656 (1992).

Comber et al, "Modulation of the Transcriptional Rate of Fcγ Receptor mRNA in Human Mononuclear Phagocytes", Cellular Immunology 145:324–338 (1992).

Cines et al, "Immune Thrombocytopenic Purpura and Pregnancy", New England Journal of Medicine 306:826–831 (1982).

Schreiber et al, "Effect of Danazol in Immune Thrombocytopenic Purpura", New England Journal of Medicine 316:503–508 (1987).

Rossman et al, "Modulation of Fcγ Receptors on the Human Macrophage Cell Line U–937", Cellular Immunology 119:174–187 (1989).

Tomer et al, "Menstrual cyclic thrombocytopenia", British Journal of Hematology 71:519–524 (1989).

Comber et al, "Receptors for the Fc Portion of Immunoglobulin G (FcγR) on Human Monocytes and Macrophages", Biochemistry of the Acute Allergic Reactions: Fifth International Symposium, pp. 273–285 (1989).

Comber et al, "Modulation of Human Mononuclear Phagocyte FcγRII mRNA and Protein", Cellular Immunology 124:292–307 (1989).

Hunter et al, "FcγRIIA–mediated phagocytosis and receptor phosphorylation in cells deficient in the protein tyrosine kinase Src", Experimental Hematology 21:1492–1497 (1993).

Darby et al, "Regulation of FcγRIII Generation of Cultured Human Monocytes", FASEB J. 4:1258 (1990).

Schreiber et al, "Autoimmune Hemolytic Anemia", Hematology 4th Ed., Eds. Nathan et al, pp. 496–510 (1993).

Bussel and Schreiber, "Immune Thrombocytopenic Purpura, Neonatal Alloimmune Thrombocytopenia, and Postransfusion Purpura", Hematology, Basic Principles and Practice, Ed. Hobbmann et al, pp. 1485–1494 (1991).

King et al, "Characterization of Fcγ Receptors on a Human Erythroleukemia Cell Line (HEL)", Exp. Hematol. 20:576–581 (1992).

Schreiber et al, "The Immunobiology of Human Fcγ Receptors on Hematopoietic Cells and Tissue Macrophages", Clinical Immunology and Immunopathology 62(1):566–572 (1992).

Rossman et al, "Modulation of macrophage Fcγ receptors by rGM–CSF", Experimental Hematology 21: (1993).

Indik et al, "Human FcγγRII: The Structure of the FcγRII Cytosolic Domain Governs Phagocytic Function", Transactions of the Association of American Physicians CV:214–221 (1992).

Brennan et al, "Binding of IgG Containing Immune Complexes to Human Neutrophil FcγRII and FcγRIII Induces Actin Polymerization by a Pertussis Toxin–Insensitive Transduction Pathway", The Journal of Immunology 146(12):4282–4288 (1991).

Ruiz et al, "In Vivo Glucocorticoid Modulation of Guinea Pig Splenic Macrophage Fcγ Receptors", J. Clin. Invest. 88:149–157 (1991).

Huang et al, "Activation of FcγRII Induces Tyrosine Phosphorylation of Multiple Porteins Including FcγRII", The Journal of Biological Chemistry 267(8):5467–5473 (1992).

Indik et al, "Calcium Signalling by the High Affinity Macrophage Fcγ Receptor Rquires the Cytosolic Domain", Immunobiol. 185:183–192 (1992).

McKenzie et al. "Characterization of the 5'–Flanking Transcriptional Regulatory Region of the Human Fcγ Receptor Gene, RcγRIIA", Molecular Immunology 29(10):1165–1174 (1992).

Schreiber et al, Immunological Diseases—Autoimmune Hemolytic Anemia—Fourth Edition, II, Ed: Samter et al, p. 1609 (1988).

Schreiber et al, Hematology—Autoimmune Hemolytic Anemia—Fourth Edition, Eds Nathan et al, p. 496 (1993).

Ruiz et al, J. Clin. Invest.—In Vivo Glucocorticoid Modulation of Guinea Pig Splenic Macrophage Fcγ Receptors— 88:149 (1991).

Schreiber et al, J. Immunology—Effect of Endogenous And Synthetic Sex Steroids on the Clearance of Antibody–Coated Cells—141:2959 (1988).

Friedman et al, J. Clin. Invest.—Effect of Estradiol and Steroid Analogues on the Clearance of Immunoglobulin G–coated Erythrocytes—75:162 (1985).

Rossman et al, Exper. Hematol.—Modulation of Macrophage Fcγ Receptors by rGM–CSF—21:177 (1993).

Ruiz et al, Clinical Res.—Macrophage Fcγ Receptor Expression: In Vivo Regulation by Human Recombinant Macrophage Colony Stimulating Factor (hrM–CSF)— 40:796A (1992).

Hunter et al, Proc. Natl. Acad. Sci.—Transfection of an Fcγ receptor cDNA induces T cells to become phagocytic— 91:10232 (1994).

Crystal, American J. Med.—Gene Therapy Strategies for Pulmonary Disease—92:6A–44S (1992).

Rosenberg et al, New England J. Med.—Gene Transfer Into Humans—Immunotherapy of Patients With Advanced Melanoma, Using Tumor–Infiltrating Lymphocytes Modified By Retroviral Gene Transduction—323:570 (1990).

Fukayama et al, J. Biol. Chem.—Respiratory Tract Gene Transfer—266:18339 (1991).

Culver et al, Human Gene Therapy—Lymphocyte Gene Therapy—2:107 (1991).

Gomez et al, New Eng. J. Med.—Impaired Function of Macrophage Fcγ Receptors and Bacterial Infection in Alcoholic Cirrhosis—311:1122 (1994).

Ruiz et al, New Engl. J. Med.—Impaired Function of Macrophage Fcγ Receptors in End–Stage Renal Disease— 322:717 (1990).

Daeron et al, Int. Immunology—Distinct Intracytoplasmic Sequences Are Required For Endocytosis And Phagocytosis Via Murine FcγRII in Mast Cells—5:1393 (1993).

Indik et al, Blood—Insertion of Cytoplasmic Tyrosine Sequences Into the Nonphagocytic Receptor FcγRIIB Establishes Phagocytic Function—83:2072 (1994).

Stribling et al, Proc. Natl. Acad. Sci.—Aerosol gene delivery in vivo—89:11277 (1992).

A. Biotinylation of membrane

B. Phosphotyrosine induction

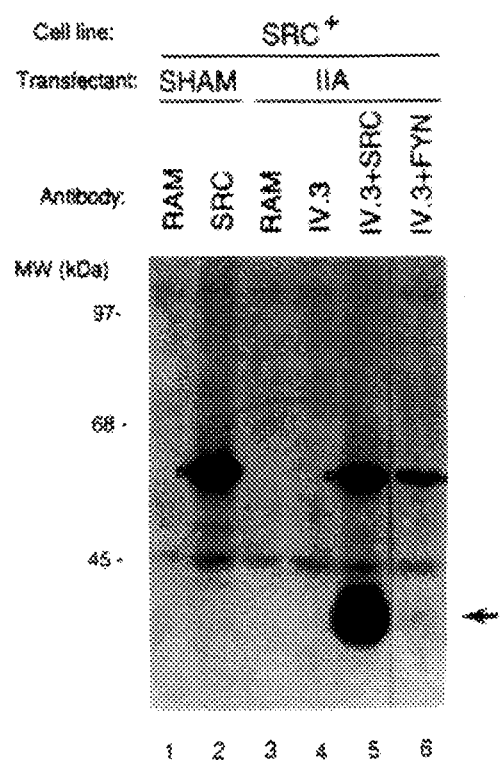
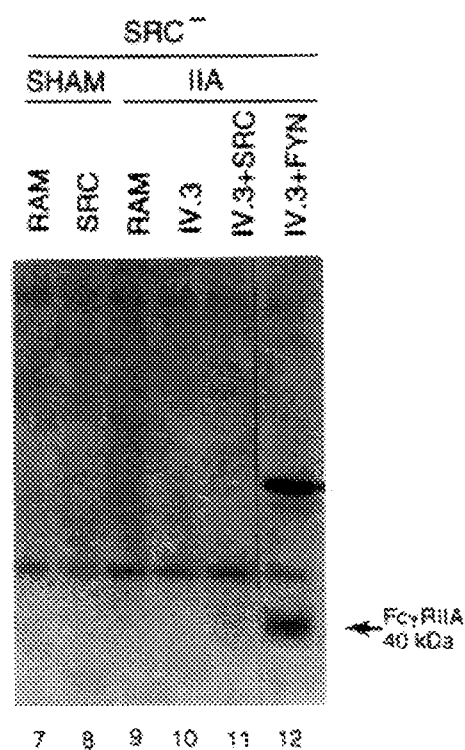

J32/FcγRIIA

J32-3.2/FcγRIIA

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ACGATGTCTA GAGGTGACTT GTCCACTCC ( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CAGGATATAG CAGAGTTGGT ACCCAGGTGG    30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CCACCTGGGT ACCAACTCTG CTATATCCTG    30

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ATGGCGAGCT CTCCGGTAAA CAGCATCTGA G    31

( 2 ) INFORMATION FOR SEQ ID NO:5:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Glu  Xaa  Xaa  Xaa  Xaa  Xaa  Xaa  Xaa  Xaa  Asp  Xaa  Xaa  Tyr  Xaa  Xaa
1                   5                        10                      15

Leu  Xaa  Xaa  Xaa  Xaa  Xaa  Xaa  Xaa  Xaa  Xaa  Xaa  Xaa  Xaa  Tyr  Xaa  Xaa  Leu
                    20                       25                       30
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /label=Xaa
            / note= "first and third Xaa is D/E; second Xaa is
            ( X a a )2,7; fourth and sixth Xaa is (Xaa)2; and fifth Xaa is (Xaa)7"

( x i ) SEQUENCE DESCRIPTION: SEQ ID NO:6:

```
Xaa Xaa Xaa Tyr Xaa Leu Xaa Tyr Xaa Leu
1               5                   10
```

( 2 ) INFORMATION FOR SEQ ID NO:7:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:7:

```
Tyr Xaa Xaa Leu
1
```

CHIMERIC IGG FC RECEPTORS

This is a divisional of application Ser. No. 08/129,391, filed Sep. 30, 1993, now abandoned.

TECHNICAL FIELD

The present invention relates, in general, to methods of stimulating phagocytosis and thereby combating infection and/or modulating immune complex disease, in particular, to methods of modulating the number and type of Fc receptors present on cells that normally possess such receptors, including monocytes and macrophages, as well as on cells that normally do not possess Fc receptors, such as fibroblasts, and to compounds and compositions suitable for use in such methods.

BACKGROUND

Mononuclear phagocytes (blood monocytes and tissue macrophages) have cell surface receptors for the Fc domain of IgG antibody. These receptors (FCγR) mediate humoral immune effector functions including phagocytosis, clearance of immune complexes and antibody-dependent cell cytotoxicity. Three classes of Fcγ receptors have been identified on human cells and characterized on the basis of size, primary structure, binding affinity for IgG subclasses, and recognition by monoclonal antibodies: FcγRI (CD64), FcγRII (CD32), and FcγRIII (CD16). FcγRI is a high affinity receptor, expressed on resting mononuclear phagocytes and stimulated neutrophils. FcγRII and FcγRIII are low affinity receptors found on a range of hematopoietic cells, including monocytes and macrophages. Macrophages express all three receptor classes while monocytes express primarily FcγRI and FcγRII.

All three classes of human Fcγ receptors have been isolated and cloned (Allen and Seed, Science 243:378 (1989); Hibbs et al, Proc. Natl. Acad. Sci. USA 85:2240 (1988); and J. Exp. Med. 166:1668 (1987)). At least two genes code for the FcγRI class of receptors (van de Winkle et al, FASEB J. 5:A964 (1991)), three genes code for the FcγRII class (designated FcγRIIA, FcγRIIB and FcγRIIC) (Brooks et al, J. Exp. Med. 170:369 (1989); Stuart et al, EMBO J. 8:3657 (1989); Qui et al, Science 248:732 (1990)) and two genes code for the FcγRIII receptor class (Simmons and Seed, Nature 333:568 (1988)).

Macrophage Fcγ receptors participate in the clearance of IgG-coated particulate and soluble antigens, including IgG-coated microorganisms, and thereby remove potentially dangerous foreign organisms. Due to their importance in host defense, functional integrity of Fcγ receptors has been studied in connection with various disease states, including autoimmune disorders (Frank et al, Ann. Intern. Med. 98:206 (1983); Kimberley and Ralph, Am. J. Med. 74:481 (1983)) and end-stage renal disease (Ruiz et al, N. Engl. J. Med. 322:717 (1990)). Macrophage Fcγ receptor function has been found to be decreased in patients with certain HLA haplotypes and in patients with the immune disorders systemic lupus erythematosus, Sjogren's syndrome and dermatitis herpetiformis (this observation was attributed to occupation of these receptors on the macrophages by immune complexes). In end-stage renal disease, macrophage Fcγ receptor function has been found to be impaired and this impairment is believed to contribute to the observed immunodepression among such patients.

Various diseases, non-bacterial in origin, are associated with a high incidence of complications due to infection. Examples of such diseases include the above-noted end-stage renal disease (Goldblum and Reed, Ann. Intern. Med. 93:597 (1980); Lahnborg et al, Transplantation 28:111 (1979); Drivas et al, Invest. Urol. 17:241 (1979); Keane and Raij, In: Drukkar et al eds. Replacement of Renal Function by Dialysis, 2nd ed., pp. 646–58 (1983)), acquired immunodeficiency syndrome (AIDS) (Bender et al, J. Infect. Disease 152:409 (1985), Smith et al, J. Clin. Invest. 74:2121 (1984)), liver disease (Rimola, In: McIntyre et al eds Oxford Textbook of Clinical Hepatology, pp. 1272–84 (1991)) and diseases of the lung, including cystic fibrosis (Gomez and Schreiber, unpublished observations) and acute respiratory distress syndrome (ARDS) (Rossman et al, Clin. Res. 41:251A (1993)). Defective Fcγ receptor-dependent clearance has been observed in certain of these diseases. Thus, there is a clear need for methods that can be used to correct defective Fcγ receptor function and/or enhance functional Fc receptor expression and thereby stimulate host defense. The present invention provides such methods and compounds and compositions suitable for use therein.

OBJECTS AND SUMMARY OF THE INVENTION

It is a general object of the present invention to provide a method of combating infection by stimulating phagocytosis.

It is the specific object of the invention to provide a method of stimulating phagocytosis by modulating the number and type of Fc receptors present on cells that normally possess such receptors, including monocytes and macrophages. In addition, it is a specific object of the invention to provide a method of combating infection by rendering cells phagocytic that do not normally possess that function, such as fibroblasts or epithelial or endothelial cells not normally expressing Fcγ receptors.

It is a further object of the invention to provide constructs suitable for use in gene therapy protocols that encode Fc receptors, and cells transformed therewith.

In one embodiment, the present invention relates to a method of increasing the phagocytic potential of cells present in a mammal that comprises introducing into the cells a DNA molecule coding for an Fc receptor. The introduction is effected under conditions such that the DNA molecule is expressed, the Fc receptor produced, and the phagocytic potential of the cells thereby increased.

In a further embodiment, the present invention relates to a method of increasing the phagocytic potential of cells of a mammal that comprises:

i) removing cells from the mammal, ii) introducing into the cells a DNA molecule encoding an Fc receptor, and iii) reintroducing the cells into the mammal under conditions such that the DNA molecule is expressed, the Fc receptor produced, and the phagocytic potential of the cells thereby increased. One skilled in the art will appreciate that steps (i)–(iii) can be carried out using methodologies known in the art.

In other embodiments, the present invention relates to a liposome comprising a DNA molecule encoding an Fc receptor, a bacterium comprising a DNA molecule encoding an Fc receptor, a T cell comprising an exogenous DNA sequence encoding an Fc receptor, and a B cell comprising an exogenous DNA sequence encoding an Fc receptor.

In yet another embodiment, the present invention relates to a DNA construct encoding an Fc receptor comprising domains, or functional portions thereof, from at least two of FcγRI, FcγRII and FcγRIII, wherein the domains, or portions thereof, are such that the receptor renders cells phagocytic that comprise same. The invention also relates to the encoded Fc receptor.

In a further embodiment, the present invention relates to a method of treating an infection comprising administering to a mammal in need of such treatment a DNA molecule encoding an Fc receptor. The administration is effected under conditions such that the DNA molecule is expressed in cells of the mammal, the Fc receptor produced, and the phagocytic potential of the cells thereby increased. The resulting cells phagocytose IgG-coated particles causing the infection, or IgG-containing soluble immune complexes derived from the infection.

Further objects and advantages of the present invention will be clear from the description that follows.

BRIEF DESCRIPTION OF THE DRAWINGS

FIGS. 3A and 3B—In vitro immune complex kinase assay of Src related tyrosine kinases from FcγRIIA infected D58 (Src+) (lanes 1–6) and SAR6 (Src−) cells (lanes 7–12). FcγRIIA-infected and sham-infected cells were lysed and cell lysates immunoprecipitated with the antibodies indicated above each lane (RAM is the rabbit-anti-mouse control, IV.3 is anti-FcγRII mAb, Src and Fyn are mAbs specific for these kinases). Immune complexes were exposed to $[\gamma^{32}P]ATP$ to allow autophosphorylation of the kinases and phosphorylation of FcγRIIA. The positions of the phosphorylated Src, Fyn and FcγRIIA proteins are indicated by the open squares, stars and arrows, respectively. Lanes 2 and 8, representing immunoprecipitates with Src antibody alone, confirm the Src+ and Src− phenotypes of the D58 and SAR6 cell lines.

DETAILED DESCRIPTION OF THE INVENTION

Figure 1A:
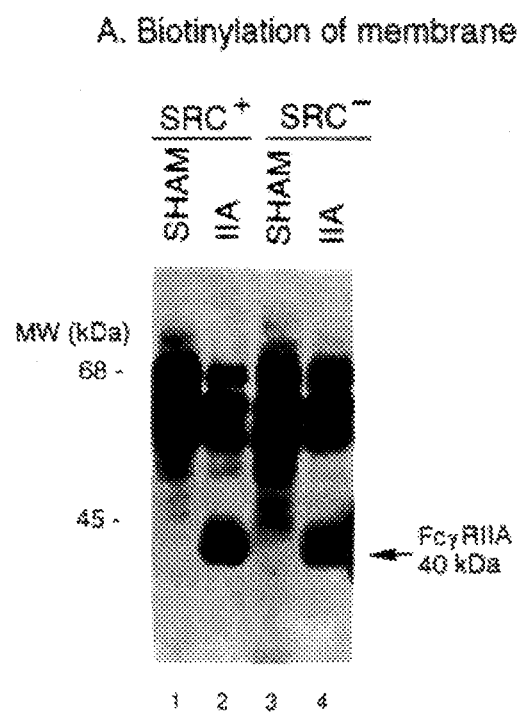
FIGS. 1A and 1B. 1A Biotinylation of D58 (Src+) and SAR6 (Src−) cells infected with FcγRIIA. Immunoprecipitation with anti-FcγRII mAb IV.3 demonstrates the 40 kD FcγRIIA protein in the membrane of FcγRIIA-infected cells (lanes 2 and 4). No receptor is present in the sham-infected cells (lanes 1 and 3). 1B Phosphorylation of FcγRIIA on tyrosine after receptor crosslinking in FcγRIIA-infected D58 and SAR6 cells. Phosphotyrosine containing proteins were immunoprecipitated from cell lysates with and without FcγRIIA stimulating (+EA and −EA). Induction of the tyrosine phosphorylated 40 KD receptor is seen in lanes 6 and 8.

The present invention relates to methods of modulating the phagocytic potential of cells that are naturally phagocytic, such as macrophages, and to methods of rendering cells phagocytic that do not naturally possess that function. In so doing, the present invention provides innovative treatment regimens that can be used to combat infections associated with various disease states.

Drug Induced Enhancement of Fcγ Receptor Expression:

In one embodiment, the present invention relates to a method of enhancing Fcγ receptor expression on phagocytic cells of a mammal, including macrophages. The method comprises administering to the mammal an active agent, such as the cytokine interferon gamma (IFN-γ), an estrogen or estrogen analog, or a hematopoietic growth factor such as granulocyte-macrophage colony-stimulating factor (GM-CSF) or macrophage colony stimulating factor (M-CSF). IFN-γ has been shown to modulate the levels of FcγRI and FcγRII apparently by increasing gene transcription. Dexamethasone has been reported to influence this IFN-γ-induced enhancement of transcription in a cell-specific manner (Comber et al, Cell. Immunol. 145:324 (1992)). Estradiol and diethylstilbesterol have been shown to facilitate clearance of IgG-coated cells (Friedman et al, J. Clin. Invest. 75:162 (1985); Ruiz et al, Clin. Res. 38:367A (1990)). GM-CSF has been shown to selectively increase monocyte FcγRII expression and function (Rossman et al, Exp. Hematol. 21:177 (1993)), and, similarly, M-CSF has been shown to increase splenic macrophage Fcγ receptors and thereby enhance the clearance of IgG-coated cells (Ruiz et al, Clin. Res. 40:796A (1992)).

One or more of the above-referenced active agents can be combined with an appropriate carrier to form a dosage form suitable for use in the method of the present invention. The amount administered will vary depending on the patient, the agent, the clinical response sought and the route of administration. Appropriate concentrations and dosage regimens can be readily determined by one skilled in the art having knowledge of these agents.

The active agents can be formulated as capsules, tablets, and the like, and as solutions and suspensions suitable for intravenous or parenteral administration. The agents can also be formulated as aerosols for administration to the lung. Carriers used are pharmaceutically acceptable and depend on the dosage form.

In vivo synthesis of the above active agents can be effected, for example, at a particular site, by introducing into cells of the patient sequences encoding the agent in an appropriate vector (e.g. an adenoviral or retrovital vector) preferably in combination with an Fcγ receptor encoding sequence (see below). In a preferred embodiment, the sequence encoding the agent encodes M-CSF and the sequence encoding the receptor encodes the γ chain of FcγRIII. Such encoding sequences can also be administered, for example, in liposomes, particularly where lung is the target tissue.

Conditions amenable to treatment by the above-noted active agents include those characterized by reduced macrophage Fcγ receptor number or function, for example, chronic renal failure, liver disease and pulmonary disorders, including acute respiratory distress syndrome (ARDS), AIDS and cystic fibrosis. Such agents can be used in combination with one or more of the therapeutic approaches described below to enhance Fcγ receptor activity and thereby treat infections that often accompany these conditions and others.

Fcγ Receptor Gene Therapy:

In a further embodiment, the present invention relates to the use of recombinant and gene therapy protocols to modulate Fc receptor expression. As noted above, genes encoding all three classes of Fcγ receptors have been isolated and cloned. All three receptor classes, FcγRI, FcγRII and FcγRIII, consist of distinct domains corresponding to their location within the cell. The cDNA structure of the FcγRII class of receptors, for example, consists of a 5' untranslated region, sequences coding for a signal peptide region (S), an extracellular domain (EC), a transmembrane region (TM), an intracytoplasmic domain (C), and a 3' untranslated region (Schreiber et al, Clin. Immunol. Immunopath., 62:S66 (1992), Cassel et al, Molec. Immunol. 30:451 (1993)). Likewise, the predicted polypeptide sequence of FcγRI shows a hydrophobic signal sequence, a hydrophobic transmembrane region and a charged cytoplasmic domain, in addition to an extracellular region that consists of three immunoglobulin-like domains, two of which share homology with the other Fcγ receptors (Allen and Seed, Science 243:378 (1989); Schreiber et al, Clin. Immunol. Immunopath., 62:S66 (1992)). FcγRIIIA is a complex consisting of a single α chain and a homo- or hetero- dimer of associated γ and ζ chains (Letourneur et al, J. Immunol. 147:2652 (1991); Ra et al Nature (Lond.) 241:752 (1989); Park et al, Clin. Res. 41:324A (1993)). Both the γ and ζ chains mediate phagocytosis, the γ chain being more efficient (Park et al, Clin. Res. 41:324A (1993)). The extracellular domain of FcγRIII is closely homologous to that of FcγRI and FcγRII, however, the transmembrane domain of FcγIII terminates in a 200–220 residue hydrophobic domain followed by four hydrophobic residues, one of which is charged (Simmons and Seed, Nature 333:568–570 (1988)). FcγRIII thus differs from FcγRI and FcγRII in that the latter two have substantial intracellular cytoplasmic domains.

FcγRI is unique among the three classes of human Fcγ receptors not only in its high affinity for IgG but also in the structure of its cytoplasmic domain. Macrophage Fc≠RII and the γ chain of FcγRIII have tyrosine residues in their cytoplasmic domains that are required for phagocytosis. In contrast, FcγRI does not contain tyrosine residues in its cytoplasmic domain (Allen and Seed, Science 243:378 (1989)) and is not phosphorylated on tyrosine. Further, FcγRI is unusual among the Ig gene family of receptors in not requiring its cytoplasmic domain for phagocytosis (Indik et al, Clin. Res. 41:170A (1993)).

Recombinant techniques make it possible to manipulate the domains of naturally occurring receptors and thereby design Fc receptors having specific characteristics. The present invention contemplates the use in gene therapy regimens of DNA sequences encoding such selectively constructed receptors, comprising domains from single or multiple Fcγ receptors, to effect the production of receptors having defined activities, both in cells that normally produce Fcγ receptors and in cells that normally do not. In the former case, the Fc receptor sequence introduced into target cells can encode a protein essentially identical to that normally produced by the cell. Alternatively, the sequence introduced can encode: i) an Fc receptor protein that is functionally comparable to, but structurally different from, the naturally occurring receptor (e.g. a protein comprising only functional portions of the domain(s) (for example, the cytoplasmic domain) of the naturally occurring receptor), or ii) a receptor protein that differs functionally and structurally from the Fc receptor that is normally present on the cell (e.g. a chimeric receptor protein comprising a high affinity FcγRI extracellular domain and transmembrane and cytoplasmic domains from FcγRIIA or FcγRIIIA). The present invention thus makes it possible to compensate for deficiencies in the production of Fc receptors of a particular functional type, which deficiencies may occur in association with a particular disease state. The invention also makes it possible to manipulate the composition of the Fc receptor population of a particular cell type. That is, a cell producing predominantly high affinity receptors can be engineered so as to produce predominantly low affinity Fc receptors.

Equally important, the present invention makes it possible to render cells phagocytic that go not normally possess that function. Sequences encoding naturally occurring Fcγ receptors or sequences encoding non-naturally occurring Fc receptors, for example, chimeric receptors that include entire domains, or functional portions thereof, from two or more naturally occurring Fcγ receptors, can be introduced into such cells. The chimeric receptors can be designed so as to take into account both the phagocytic potential of the cells into which the encoding sequences are to be introduced and the receptor domain properties suited for achieving the desired therapeutic effect. While not all cells are equally suitable as recipients for all Fc receptor-encoding constructs, operability can be readily assessed using in vitro model systems such as those described by Indik et al (J. Clin. Invest. 88:1766 (1991) and Hunter et al, Clin. Res. 41:244A (1993); see also Amigorena et al, Nature (Lond) 358:337 (1992); Park et al, Clin. Res. 41:324A (1993); Toijman et al, Blood 79:1651 (1992); Kruskal et al, J. Exp. Med. 176:1673 (1992); (see also Examples below)). This embodiment of the invention may be particularly advantageous since cells, such as fibroblasts, that are rendered phagocytic may injest particles without releasing significant quantities of superoxide radicals or toxic biologically active products. This is in contrast to cells that are normally phagocytic, such as macrophages. One skilled in the art will appreciate that a reduction in the release of toxic products results in a reduction in the possibility of inflammation.

Constructs:

Chimeric Fc receptors suitable for use in the present invention include those prepared as detailed in the Examples below. For instance, single chain chimeras of the α and γ chains of FcRIIIA can be prepared. Sequences encoding such chimeras have been introduced into COS-1 cells and the phagocytic potential conferred examined. For example, a DNA sequence encoding the extracellular domain of the α chain of Fcγ RIIIA, the transmembrane domain of the γ chain of FcγRIIIA or FcγRI and the cytoplasmic domain of the γ chain of FcγRIIIA has been transfected into COS-1 cells (the transmembrane domain of the α chain of FcγRIII can be used in lieu of that of the γ chain, though perhaps not as effectively). Such chimeras display phagocytic activity in the COS-1 assay system though not at a level equivalent to the multichain form of FcγRIIIA. In spite of the reduced activity, single chain constructs are clearly advantageous in view of the difficulties inherent both in introducing into target cells multiple sequences and in achieving proper complexation of the encoded proteins.

Fc chimeric receptors have also been prepared from a combination of domains of FcγRII isoforms and from a combination of FcγRI and FcγRII domains. Specifically, a chimetic receptor comprising the extracellular and transmembrane domains of FcγRIIB2 and the cytoplasmic domain of FcγRIIA has been shown to confer phagocytic potential on host cells, thus demonstrating that the FcγRIIB2 transmembrane domain is capable of transmitting the phagocytic signal to the FcγRIIA cytoplasmic domain (FcγRIIB receptors do not themselves confer phagocytic potential). Similarly, a chimeric receptor comprising the extracellular domain of FcγRI and the transmembrane and cytoplasmic domains of FcγRIIA has been shown to induce phagocytosis in host cells. In contrast, chimeras comprising the extracellular domain of FcγRI and the transmembrane domain of FcγRI or FcγRIIA do not result in phagocytosis when the cytoplasmic domain is from FcγRIIA or FcγRI, respectively. However, chimeras comprising the extracellular domain of FcγRI, the transmembrane domain of FcγRI and the cytoplasmic domain of the γ chain of FcγRIII, do result in phagocytosis. It will be appreciated that chimeras comprising the extracellular domain of FcγRI (and appropriate transmembrane and cytoplasmic domains) can be advantageous in view of the high binding affinity of the FcγRI extracellular region.

Chimeras in addition to those described above and detailed below are contemplated. For example, the cytoplasmic domain of FcγRIIA can be used in combination with the extracellular domain of FcγRI and the transmembrane domain of FcγRIIA. Further, the extracellular and transmembrane domains of FcγRI or FcγRII can be used in combination with the cytoplasmic domain of the γ chain of FcγRIII. Further, chimeras of the invention can include the extracellular domain from FcγRIIA, FcγRI or from the α chain of FcγRIII, the transmembrane domain from FcγRIIA or from the α or γ chain of FcγRIII, and the cytoplasmic domain of either the γ chain of FcγRIII or FcγRIIA (e.g., i) the extracellular and transmembrane domains of FcγRIIA, ii) the extracellular domain of the α chain of FcγRIII and the transmembrane domain of the γ chain of FcγRIII, or iii) the extracellular domain of FcγRI and the transmembrane domain of the α or γ chain of FcγRIII—each with the cytoplasmic domain from either the γ chain of FcγRIII or FcγRIIA (it is noted that preliminary results suggest that certain chimeras comprising the transmembrane domain of the α chain of FcγRIII may not be operative).

While chimeras of the invention can include the entire extracellular, transmembrane and cytoplasmic domains of the respective naturally occurring receptors, such is not necessarily the case. Rather, the chimeras can comprise only the functional portion(s) of the respective domains. For example, in the case of the cytoplasmic domain of FcγRIIA, truncation at amino acid 303 (which results in deletion of the terminal 8 amino acids but preservation of the two tyrosine (Y282 and Y298)-containing core sequences important in phagocytosis does not decrease phagocytosis (Mitchell et al, Clin. Res. 41:1894A (1993)). Truncation of the FcγRIIA cytoplasmic domain at amino acid 268 or 280, however, results in receptors lacking the tyrosines at positions 282 and 288, and lacking phagocytic activity. These data are consistent with the importance of tyrosine residues in the cytoplasmic Fc receptor domain in transmission of the cytoplasmic signal. In treatment regimens in which suppression of phagocytic potential is advantageous (for example, autoimmune diseases) these later mutants or peptides derived from or mimicking these mutants can be useful (see the commonly owned application entitled "Method of Inhibiting Phagocytosis" filed concurrently herewith, the entire disclosure of which is incorporated herein by reference). It will be appreciated, however, that when potentiation of phagocytosis is sought, functionality of each of the domains must be preserved. In this regard, it appears that the second YX2L of the core sequence of the cytoplasmic domain of FcγRIIA (E-X8-D-X2-Y-X2-L-X12-Y-X2-L) (SEQ ID NO:5) and the γ chain of FcγRIIIA (D/E-X2,7-D/E-Y-X2-L-X7-Y-X2-L) (SEQ ID NO:6) are particularly important for phagocytosis (note also that the exon 3 domain of the γ chain of FcγRIII that is 5' or amino terminal to the Y-X2-L (SEQ ID NO:7) motif appears to play a role in phagocytosis since its elimination diminishes phagocytosis by the γ subunit of FcγRIIIA) (the numbers following the letter X denote the number of amino acids at that position; X can be any amino acid but X within a Y-X2-L preferably represents the amino acids present in the Y-X2-L sequence of the cytoplasmic domain of FcγRIIA or the γ chain of FcγRIII). Accordingly, it can be expected that phagocytosis can be increased by multiplying the number of copies of the core sequence, for example, in FcγRIIA or in the γ chain of FcγRIIIA, or by multiplying the number of copies of the second Y-X2-L present in those core sequences. The specific amino acids in this second Y-X2-L are important for phagocytosis and appear to provide specificity to the phagocytic signal. It is also expected that phagocytic activity can be increased (as compared to the wild type gamma chain) by, for example, inserting the FcγRIIA second Y-X2-L into the γ chain of FcγRIIIA (as compared to the wild type gamma chain). Furthermore, it is expected that inserting the second cytoplasmic domain Y-X2-L of the γ chain of FcγRIIIA (or both the first and second cytoplasmic domain Y-X2-L of the γ chain) into the ζ chain of FcγRIIIA will increase the phagocytic activity of the ζ chain. Further, the inclusion of two additional Y-X2-L or Y-X3-I motifs to FcγRIIB (which itself is non-phagocytic) renders this receptor phagocytic (this includes adding a variation of the Y-X2-L, Y-X3-I, to the carboxyterminal portion of the cytoplasmic domain). As indicated above, fibroblasts and fibroblast-like cells (for example, COS cells) can be used to assess the operability of a particular receptor construct.

The above-described chimeras of the invention can be constructed by the polymerase chain reaction (PCR) (Horton et al, Biotechniques 8:528 (1990)) using as templates appropriate receptor cDNA and appropriate oligonucleotides. PCR products can be directly cloned into an expression vector, for example, pSVL, and confirmed by complete sequencing. The expression of the chimeric receptors can be assayed by flow cytometry using anti-Fcγ receptor mAbs and phagocytic function can be evaluated following incubation of IgG-sensitized RBCs.

More specifically, two step overlap extension PCR, a technique that allows introduction of mutations into any part of a PCR fragment, can be used to generate the chimeric molecules of the invention, as well as the mutated/truncated receptors described herein. In the first step in overlap extension PCR, two primer pairs, 1a and 1b and 2a and 2b, are used to generate two overlapping fragments, 1 and 2. In step 2, when these two fragments are mixed, denatured and reannealed, the 3' end of the sense strand of fragment 1 anneals to the 3' end of the antisense strand of fragment 2. This overlap can be extended to form the entire recombinant product and can be amplified by PCR using primers 1a and 2b. The overlap region is determined by primers 1b and 2a and can contain any sequence as long as parts of the oligomers are complementary. This region is where base changes are incorporated when the technique is used for site directed mutagenesis. Alternatively, the overlap can be designed to make a clean joint between two fragments from two different DNA molecules to form a chimetic molecule. For construction of chimeric mutants, primers 1b and 2a are designed to contain regions from both contributing molecules so that fragments 1 and 2 can anneal. For example, to construct the chimera containing the FcγRIIIAα extracellular region and the transmembrane and cytoplasmic domains of the γ chain, the following 2 pairs of oligomer primers are used (primer 1b is shown 3'-5'):

1a. 5'ACGATGTCTAGAGGTGACTTGTCCACTCC3'(SEQ ID NO:1)(sense)

1b. 3'GGTGGACCCATGGTTGAGACGATATAGGAC5'(SEQ ID NO:2)(antisense)

2a. 5'CCACCTGGGTACCAACTCTGCTATATCCTG3'(SEQ ID NO:3)(sense)

2b. 5'ATGGCGAGCTCTCCGGTAAACAGCATCTGAG3'(SEQ ID NO:4)(antisense)

Xba1 and Sac1 restriction sites can be introduced in primers 1a and 2b respectively so that the final PCR product encoding the chimeric receptor can be ligated in the proper orientation into, for example, an SV40 based expression vector (e.g., PSVL) restricted with Xba1 and Sac1. To produce truncated molecules, stop codons can be introduced via primers 1b and 2a. In a similar fashion, tyrosine codons can be replaced by phenylalanine codons and serine or threonine codons by alanine codons.

Target cells and modes of administration:

As noted above, the present invention can be used to treat patients that are predisposed to an increased risk of infection. Such patients include, but are not limited to, those suffering from liver disease resulting, for example, from alcoholic cirrhosis, from kidney disorders, such as end-stage renal disease, and from pulmonary disorders including cystic fibrosis and ARDS. AIDS patients are also appropriate candidates for treatment in accordance with the present invention. In each instance, treatment is effected by increasing the phagocytic potential of cells of the patient.

In the case of pulmonary disorders, the receptor-encoding sequence can be administered to the cells of the lung, including macrophages, in the form of an aerosol. The encoding sequence can be present in the aerosol as a particle (e.g. liposome or non-infectious bacteria, for example, Listeria) that is phagocytosed by the pulmonary macrophages. The encoding sequence can also be present in a vital vector.

Viral vectors can also be used to introduce the Fc receptor-encoding sequence of the invention into cells of the pulmonary tree, including fibroblasts, epithelial cells and other cells present in the lung. The vectors can be introduced as an aerosol and can take the form of a replication defective herpes or adenoviral vector. Retroviral vectors can also be used, as well as other viral vectors. (See, generally, Bajocchi et al, Nat. Genet. 3:229 (1993); Lemarchand et al, Circ. Res., 72:1132 (1993); Ram et al, Cancer Res. 53:83 (1993); Crystal, Am. J. Med. 92:44s (1992); Yoshimura et al, Nucl. Acids Res. 20:3233 (1992); Morecki et al, Cancer Immunol. Immunother. 32:342 (1991); Culver et al, Hum. Gene Ther. 1:399 (1990); Culver et al, Transplant. Proc., 23:170 (1991)).

The Fc receptor-encoding sequences of the invention can also be introduced into cells such as T cells thereby rendering them phagocytic. The advantages of phagocytic T cells are clear, particularly in combating infections that accompany diseases such as AIDS. The abundance of T cells is such that by transforming them with the Fc receptor encoding sequences of the invention, the phagocytic capacity of the blood is substantially increased.

T cells can be rendered phagocytic by transforming them in vitro with, for example, a vital vector containing a sequence encoding an Fc receptor (e.g. FcγRIIA). Techniques such as electroporation can also be used. The transformed T cells can then be reintroduced into the patient from which they were derived. Example X details the transformation of T-cells with FcγRIIA and the results presented demonstrate that phagocytic activity is conferred on these cells. In addition, FcγRIIA is phosphorylated in the T-cells when activated, similar to the phosphorylation observed in activated monocytes and macrophages. FcγRIIA activation in these T-cells leads to tyrosine kinase activation and phosphorylation. The T-cell tyrosine kinase ZAP-70 is activated (phosphorylated) upon FcγRIIA activation in T-cells. B lymphocytes are less abundant than T lymphocytes, but they too can be rendered phagocytic using similar protocols (see Example VII).

Further, blood monocytes can be transformed ex vivo with the receptor-encoding sequence of the invention (using, for example, physical techniques such as electroporation, or vectors, including viral vectors (e.g., retroviral vectors, adenoviral vectors, or herpes viral vectors); liposomes and Listeria can also be expected to be useful in transforming monocytes and then reintroduced into the patient). This protocol is particularly advantageous when the liver or spleen is the target site.

In addition to the above, the present invention can be used with patients suffering from immune complex diseases such as lupus erythematosus and rheumatoid arthritis to increase local clearance of circulating immune complexes so as to prevent their deposition in tissues, such as the kidney, and in the joints. This increase can be effected by stimulating liver and splenic macrophage phagocytic potential using protocols such as those described herein.

It will be appreciated from a reading of the foregoing that, depending on the target cell and the effect sought, various methods can be used to introduce receptor-encoding sequence into the cell (in addition to electroporation noted above, calcium phosphate as well as other techniques can be used to introduce naked DNA). It will also be appreciated that the gene therapy approach to enhancing phagocytic potential can be used alone or in combination with the drug therapy approach described above. The combination therapy makes it possible to increase the number of naturally occurring receptors and at the same time effect the selective expression of receptors of a particular functional type.

The following non-limiting Examples describe certain aspects of the invention in greater detail.

EXAMPLE I

In Vivo Administration of hrM-CSF Increases Splenic Macrophage Fcγ Receptors Human recombinant macrophage colony stimulating factor (hrM-CSF) was studied in vivo using an established model in the guinea pig (Schreiber et al, J. Clin. Invest. 51:575 (1972)). Adult male guinea pigs were treated for 5 days with hrM-CSF (500 µg/kg) and splenic macrophage FcγR function and protein expression were assessed by i) the splenic macrophage clearance of IgG sensitized $^{51}$Cr-guinea pig RBC (EA), ii) the in vitro binding of EA by isolated splenic macrophage, and iii) FACS analysis using monoclonal antibodies with specificity for the two guinea pig splenic macrophage Fcγ receptors, FcγR1,2 and FcγR2. Treatment with hrM-CSF enchanced the clearance of EA by 72 ±5%. In addition, a greater proportion of isolated splenic macrophages from hrM-CSF treated animals bound EA in vitro: 80±7% vs 48±4%(sham), p<0.001. In vivo hrM-CSF increased the expression of both splenic macrophages Fcγ receptors: 81±6% and 130±10% for FcγR1,2 and FcγR2, respectively. The lowest effective dose of hrM-CSF was 250 µg/kg, increasing the expression of FcγR1,2 by 26±3% and FcγR2 by 42±4%. At this dose, the clearance of EA was also enhanced. The effect of hrM-CSF required at least 4 days of treatment.

EXAMPLE II

FcγIIA Mediates Phagocytosis and Receptor Phosphorylation in a Fibroblast Cell Line Experimental Protocols:

Cell culture and reagents:

The SAR6 cell line was derived from primary embryonic mouse fibroblasts in which both Src alleles had been disrupted by homologous recombination using the neomycin resistance gene (Thomas et al, Science 254:568 (1991)). D58 was derived from primary embryonic mouse fibroblasts that were wild type for Src. Cells were maintained in DMEM containing glucose (4.5 mg/ml), glutamine (25 mg/ml), penicillin (100 U/ml), streptomycin (100 µg/ml) and 10% heat inactivated fetal calf serum.

Retroviral infections:

FcγRIIA was inserted into the HindIII site of the retroviral vector pLCX (Miller and Rosman, Biotechniques 9:908 (1989)) under control fo the CMV promoter. The resulting construct, pLNCX2A, was transfected into the ecotropic packaging cell line, Psi2. Two days after transfection, the cells were diluted 1:20 and G418 resistant colonies were isolated and assessed for virus production. The stock gave 1×10 G418 resistant colonies per milliliter. 0.1 ml of vital stock was used to infect DS8 and SAR6 cells (2.5×10 cells per infection). Twenty four hours after infection, the cells were diluted 1:3 and allowed to reach 80–90% confluence before assaying for cell surface expression of FcγRIIA and for phagocytosis. Transient infections were carried out due to the fact that the G418 resistant phenotype of the SAR6 cell line prohibited the selection of stable lines using this retroviral vector.

Flow cytometry:

To determine the extent of FcγRIIA expression on the cell surface of infected D58 and SAR6 cells, samples were stained with fluorescein-labeled anti-FcγRII mAb (IV.3) or with an isotype control (Indik et al, J. Clin. Invest. 88:1766 (1991)). Fluorescence was measured on a FACStar (Becton-Dickinson, Mountainview, Calif.). 10,000 events were analysed in each case and mean fluorescence intensities were estimated and contour maps were generated using Consort 30 software.

Binding and phagocytosis of IgG-sensitized sheep red blood cells (EA):

EA was prepared as described previously (Indik et al, J. Clin. Invest. 88:1766 (1991)), overlaid onto the infected cells and incubated at 37° C. for 30 minutes. Unbound EA was removed by washing with PBS and the plates stained with Wright-Geimsa to assess rosetting. To determine phagocytosis, extracellular bound EA was removed by exposure to hypotonic buffer before staining with Wright-Geimsa.

Biotinylation of cell membranes:

Twenty four hours after infection, FcγRIIA-infected and sham-infected SAR6 and D58 cells were plated on 100 mm petri dishes. After a further twenty four hours, the cells (2×10) were washed once with PBS, overlaid with 1.0 ml of PBS containing 100 µl of 1M NaHCO and 100 ml of 1 mg/ml biotin (Pierce, Rockford, Ill.) and incubated at room temperature for 60 minutes. One hundred µl of NHCl was added and incubation continued for a further 10 minutes. The cells were washed once with PBS and lysed with 1.0 ml RIPA buffer (1% Triton X-100, 1% sodium deoxycholate, 0.1% SDS, 158 mM NaCl, 10-mM Tris pH7.2, 5 mM NaEGTA, 1 mM phenylmethylsulphonyl fluoride, 1 mM NaVO) at 4° C. for 30 minutes. FcγRIIA was immunoprecipitated from the biotinylated cell membrane extract with anti FcγRII mAb (Eisman and Bolen, Nature 355:78 (1992)) and analyzed on a 7.5% SDS-polyacrylamide gel (PAGE). Immunoblots were probed with avidin-horseradish peroxidase (BioRad, 1:1000 dilution), followed by Enhanced Chemiluminescence reagents (Amersham Corp.) and visualized using Kodak XAR-5 film.

Phosphotyrosine immunoblots:

FcγRIIA-infected and sham-infected D58 and SAR6 cells (2'10 cells per 100 mm petri dish) were overlaid with 500 µl EA and incubated at 37° C. for 30 minutes to activate FcγRIIA. After washing with PBS to remove unbound EA, the bound EA was removed by exposure to hypotonic buffer. Cells were lysed on the plates with 1.0 ml RIPA buffer at 40° C. for 30 minutes and phosphotyrosine containing proteins were immunoprecipitated from the cell lysates using polyclonal rabbit antisera UP28 (Huang et al, J. Biol. Chem. 267:5467 (1992)). The immunoprecipitates were analyzed on a 7.5% SDS-PAGE and immunoblots probed with antiphosphotyrosine mAb, 4G10 (Huang et al, J. Biol. Chem. 267:5467 (1992)).

In vitro immune complex kinase assay of Src-family protein tyrosine kinases from FcγRIIA infected Src− and Src+ cells:

FcγRIIA-infected and sham-infected SAR6 and D58 cells (2'10 cells per 100 mm petri dish), were lysed with 1.0 ml RIPA buffer at 4° C., for 30 minutes. Immunoprecipitations were performed by mixing cell lysates with the following mAbs singly or in combination: anti-Src (Lipsiche et al, J. Virol. 48:352 (1983)), anti-FcγRII (Rosenfeld et al, J. Clin. Invest. 76:2317 (1985)), anti-Fyn (Huang et al, J. Biol. Chem. 267:5467 (1992)) and rabbit anti-mouse (RAM) IgG. The immune complexes were incubated with [γ$^{32}$P]ATP to allow autophosphorylation of the kinases and phosphorylation of the substrate and were separated by SDS-PAGE. The gel was washed with 1N KOH at 55° C. for two hours to remove serine/threonine phosphorylation (tyrosine phosphorylation is relatively resistant to alkali) before exposure to Kodak XAR-5 film.

Figure 2A:
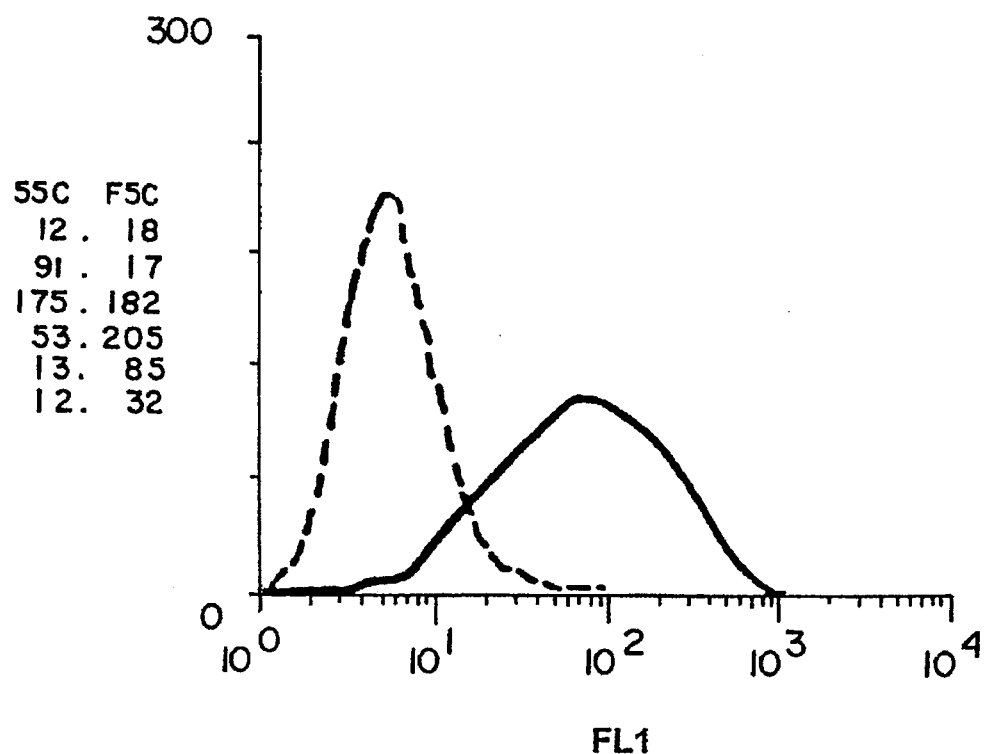
FIGS. 2A and 2B—Fluorescence histograms of (a) D58 and (b) SAR6 cells infected with FcγRIIA. The dotted line represents cells stained with an isotype control mAB and the solid lines represent cells stained with anti-FcγRII.
Figure 2B:
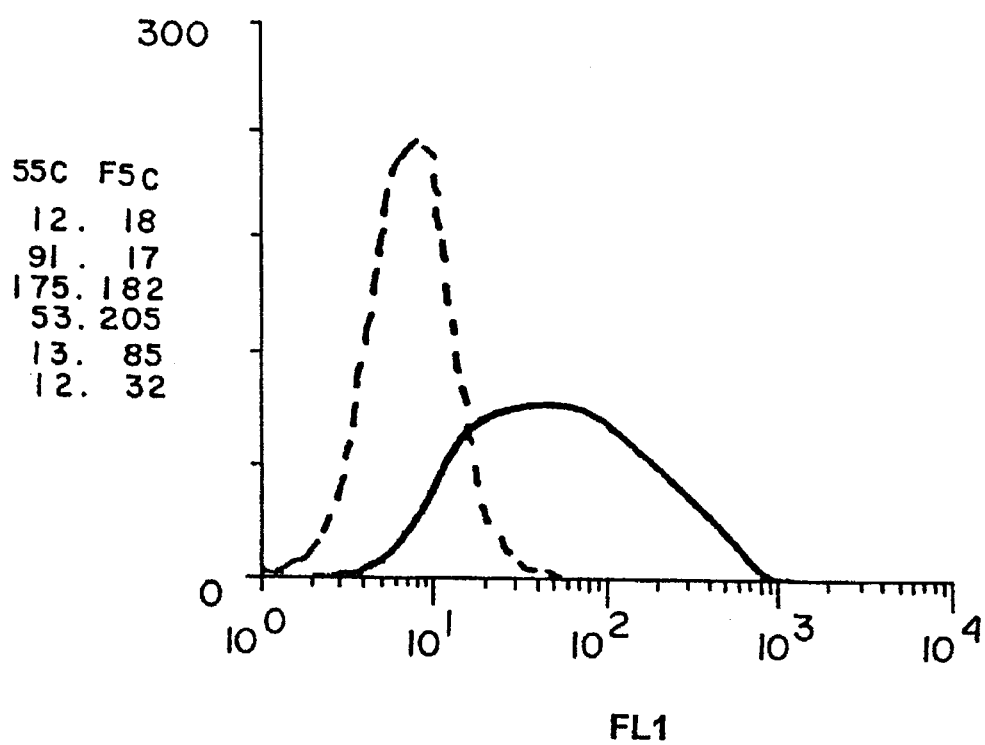

Results of Phagocytosis and Phosphorylation Studies:

Forty eight hours after infection of cell lines D58 and SAR with a retroviral vector containing a FcγIIA encoding sequence, cell surface biotinylation followed by immunoprecipitation with anti-FcγRII mAb demonstrated that the 40 kD receptor was present in the membrane of both Src+ and Src− cells (FIG. 1A). Fluorescence histograms of FcγRIIA infected SAR6 and D58 cells are shown in FIGS. 2A and B. In this representative experiment, sixty five percent of cells expressed the receptor in SAR6 and eighty one percent in D58 with mean fluorescence intensities of ninety five and one hundred and fifty one, respectively. Both Src− and Src+ cells incubated with IgG sensitized cells (EA) bound and phagocytosed these immune complexes. Forty three percent of cells phagocytosed EA in the Src− mutant and seventy percent in D58. In contrast, no binding or phagocytosis was observed in sham infected cells.

Figure 1B:
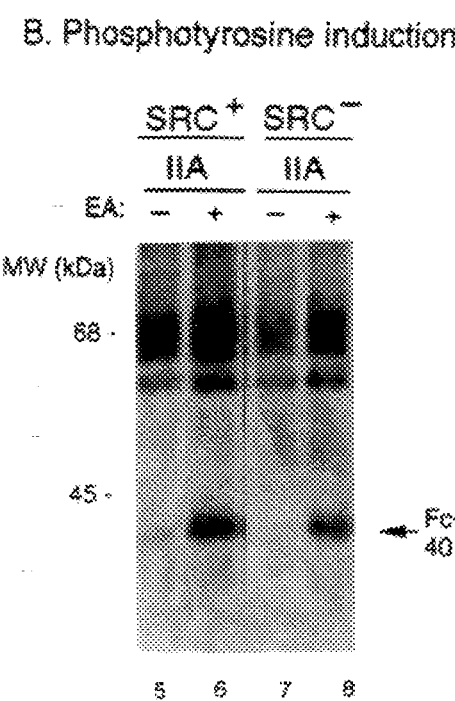

To determine if the activated receptor was phosphorylated in the Src− cell line, phosphotyrosine containing proteins were immunoprecipitated from activated and unactivated SAR6 and D58 infected cells. Crosslinking of FcγRIIA with EA resulted in tyrosine phosphorylation of the 40 kD FcγRIIA receptor protein in both Src+ and Src− cells (FIG. 1B).

Although Src is not responsible for phosphorylating FcγRIIA in SAR6 cells, FcγRIIA in these mouse fibroblasts was able to act as a substrate for Src related tyrosine kinases. An in vitro immune complex kinase assay was performed on lysates from SAR6 and D58 cells that had been infected with FcγRIIA. Lysates were co-immunoprecipitated with antibodies specific for the receptor protein and with antibodies specific for either Src or Fyn kinases (FIGS. 3A and 3B). The co-immunoprecipitates were incubated with [γ$^{32}$P] ATP to allow autophosphorylation of the kinase and phosphorylation of FcγRIIA. FcγRIIA was phosphorylated by Src in this in vitro assay (FIG. 3A, lane 5). Fyn could also phosphorylate FcγRIIA, although to a lesser extent when compared to Src (lane 6). In the absence of the kinases, no phosphorylation of FcγRIIA was observed (lanes 4 and 10) consistent with the lack of tyrosine kinase sequences in the receptor. In the Src− lysates, co-immunoprecipitation with Src and FcγRIIA did not result in phosphorylation of the receptor (lane 11), but a low level of phosphorylation of FcγRIIA was observed in co-immunoprecipitates of FcγRIIA and Fyn (lane 12). This may reflect the efficiency of phosphorylation of the receptor by Fyn; alternatively the fibroblasts may express different amounts of the two kinases.

EXAMPLE III

High Affinity Fcγ Receptor (CD64) Induces Phagocytosis in the Absence of its Cytoplasmic Domain Wild type (WT) and a mutant (MT) FcγRI, engineered to omit the cytoplasmic domain (CYT), were transfected into COS cells and murine macrophages (P388D1). The phagocytic potential of the transformed cells was assessed using IgG-coated RBCs (EA) and RBCs conjugated with Fab anti-human FcγR1 mAb (E-mAb). FcγR1, in contrast to FcγRII, did not induce phagocytosis in COS cells (assessed by electron microscopy) but did induce a Ca$^{2+}$ signal which required its CYT. However, both WT and MT FcγRI induced phagocytosis in P388D1. Phagocytosis by WT FcγRI was inhibited by the tyrosine kinase inhibitor tyrphostin 23. Furthermore, activation of FcγRI on monocytes with Fab anti-FcγRI induced tyrosine phosphorylation of FcγRII, determined by antiphosphotyrosine immunoblots. FcγR1 thus mediates a Ca$^{2+}$ signal through its cytoplasmic domain but not phagocytosis. FcγRI induced phagocytosis therefore requires elements, present in macrophages but absent in COS cells, that permit transmembrane communication.

EXAMPLE IV

Structural Requirements of the Human Fc Receptor FcγRIIA in Phagocytosis

The structural requirements of FcγRIIA in phagocytosis were examined using COS-1 cells, which lack endogenous Fc receptors, as the recipient in transfection studies. FcγRIIA has two (Y282 and Y298) tyrosine-containing core sequences, Y-X2-L, within a cytoplasmic motif similar to that in other Ig gene family receptors. Truncation of the cytoplasmic domain at amino acid 268 or 280, to produce mutants lacking both these tyrosines and both core sequences, eliminated phagocytic activity even though these transfectants bound IgG-sensitized cells efficiently. Truncation at amino acid 303, deleting only the terminal 8 amino acid and preserving both core sequences, did not decrease phagocytosis. Substitution of Y282 with phenylalanine (F) inhibited phagocytosis and substitution of Y298 with F partially diminished the phagocytic signal. Substitution with F of the third cytoplasmic tyrosine (Y275) outside the conserved motif did not alter phagocytosis. Replacement of Y282 or Y298 with lysine reduced phagocytosis further, but replacing Y275 with lysine had little effect. Replacement by F of either Y275 or Y298 in combination with Y282 completely eliminated phagocytic function, suggesting that they interact with Y282 in transmission of the signal. In contrast, some phagocytic activity was preserved in mutants containing Y282, but with F at Y275 and Y298. Deletion of T284-L285 within the Y282MTL core sequence also diminished phagocytosis. The two core Y282-X2-L and Y298-X2-L sequences contain an intervening stretch of amino acids with 2 prolines suggesting an intervening non-helical structure. A mutant, Δ287–291, in which 5 amino acids including the 2 prolines were deleted reduced phagocytic function. The initial core cytoplasmic sequence Y282MTL and the proline containing region between Y282 and Y298 are important for transmission of the phagocytic signal by FcγRIIA.

EXAMPLE V

The Structure of the γ chain Fc Receptor Subunit Determines Phagocytic Function of Macrophage FcγRIII (FcγRIIIA)

A FcγRIIIA encoding sequence was transfected into COS-1 cells to study its phagocytic function, determined by electron microsopy, in the absence of other Fc receptors. Co-transfectants of FcγRIIIA-α with either γ or ζ gave equivalent cell surface expression and binding of IgG-coated cells (EA), but γ was 6 fold more effective than ζ in phagocytosis. To delineate the region of the γ chain important in phagocytosis, two deletion mutants, were constructed, deleting the C-terminal 7 amino acids or deleting the C-terminal 22 amino acids which have a tyrosine containing conserved motif, Y-X2-L-X7-Y-X2-L, present in several Ig gene super family receptors. The C-terminal 7 amino acid deletion demonstrated minimally reduced phagocytic activity, whereas the more extensive deletion completely eliminated phagocytosis, suggesting the importance of the conserved cytoplasmic motif. The role of the conserved cytoplasmic tyrosines was then examined. Conservative substitution by phenylalnine of either of the 2 cytoplasmic tyrosines in the γ chain significantly decreased $Ca^{2+}$ signaling and reduced phagocytosis by >99%. Tyrophostin 23 which alters tyrosine kinase activity reversibly inhibited phagocytosis, indicating that phosphorylation of γ and/or downstream protein tyrosine kinase(s) is required for a phagocytic signal. Further, single chain Fcγ receptor chimeras, consisting of the γ cytoplasmic domain and the α extracellular domain with the transmembrane domain of either FcγRIIIA-γ or FcγRI were able to mediate a phagocytic signal. However, single chain chimeras were not sufficient for full phagocytic activity.

EXAMPLE VI

Examination of Phagocytosis by Chimeric Fcγ Receptors

FcγRIIA avidly binds and phagocytoses IgG-sensitized cells (EA), as assessed by electron microsopy using the COS cell transfection model system, but FcγRI and two other FcγRII isoforms, FcγRIIB1 and FcγRIIB2, do not transmit a phagocytic signal although they also bind EA avidly. Chimeric receptors of FcγRI and FcγRII were constructed in order to further assess the function of their transmembrane and cytoplasmic domains in phagocytosis. Chimeric transfectants consisting of the extracellular (EC) and transmembrane (TM) regions of FcγRIIB2 and the cytoplasmic domain (CYT) of FcγRIIA and chimeric transfectants consisting of the EC of FcγRI and the TM and CYT of FcγRIIA were efficient in phagocytosis. In contrast, phagocytosis was greatly diminished by chimeras consisting of the EC and TM of FcγRI and the CYT of FcγRIIA. In addition, a chimeric transfectant bearing the EC from FcγRI, the TM from FcγRIIA and the CYT from FcγRI did not phagocytose EA. These studies indicate that in this system: i) the transmembrane domain of FcγRIIB2 is able to provide the necessary structure to permit a phagocytic signal by the cytoplasmic domain of FcγRIIA, ii) the transmembrane domain of FcγRI is unable to transmit a phagocytic signal to the cytoplasmic domain of FcγRIIA, and iii) the transmembrane domain of FcγRIIA is unable to confer phagocytic competence to FcγRI.

EXAMPLE VII

B-Cell Antigen Receptor Subunit Ig-γ Mediates Phagocytic Signal

The B-cell receptor complex is composed of an antigen recognition subunit noncovalently associated with a membrane subunit consisting of heterodimers of two chains, Ig-α and Igβ/γ, which are products of the mb-1 and B29 genes. Both membrane Ig subunits contain within their cytoplasmic regions a conserved sequence implicated in intracellular signalling. Using COS cell transfectants, the Fc receptor FcγRIIA, which is not present in B-cells, has been shown to mediate a phagocytic signal and to contain within its cytoplasmic domain a sequence similar in some aspects to that of Ig-α. Therefore, a FcγRIIA and Ig-α chimera was constructed, consisting of the extracellular and transmembrane domains of FcγRIIA and the cytoplasmic domain of Ig-α. This chimeric receptor was expressed in COS-1 cell transfectants, determined by flow cytometry, and bound IgG-sensitized RBCs (EA) efficiently. Furthermore, transfection of this chimeric receptor into COS-1 cells conferred phagocytic competence to COS-1 cells similar in extent to transfection of the receptor FcγRIIA.

EXAMPLE VIII

Alterations in Monocyte/Macrophage Fcγ Receptor Expression in the Acute Respiratory Distress Syndrome (ARDS)

Monocytes from patients with ARDS were used to examine potential alterations in Fcγ receptor expression. Since macrophages may express all 3 classes of Fcγ receptors, specific mAbs for each class of Fcγ receptor and flow cytometry were used to quantitate Fcγ receptor expression. Patients with ARDS met the following four criteria: i) acute bilateral alveolar-type infiltrates on chest radiograph, ii) severe hypoxemic respiratory failure with PaO/FiO </=150 without PEEP, iii) absence of congestive heart failure, and iv) having a presumed pre-disposing cause of ARDS. Seven patients with ARDS were compared to 5 normal controls. Whether measured as percent of cells expressing the Fcγ receptor or the difference in mean fluorescence intensity (MFI), FcγRI was reduced in patients with ARDS (ARDS= 36.0±6.3% [mean±SEM] or 22.6±7.0 MFI; normal= 52.8±11.3% or 35.6±6.4 MFI) and FcγRIII was increased (ARDS =15.6±7.9% or 12.1±4.9 MFI; normals=0.8±0.6% or 1.4±1.2(MFI). No correlation was observed between decreased FcγRI and increased FcγRIII expression, suggesting differential regulation of these receptors in vivo. No significant change was observed in the expression of FcγRII. Four of seven patients with ARDS died. One patient was restudied following recovery and Fcγ receptors returned to normal values.

EXAMPLE IX

Fc Receptor Defect in Patients with Liver Disease

Experimental Protocols:

Patients:

Forty nine patients (16 women and 33 men) whose mean (±SD) age was 55.2±8.3 years were studied. All patients had biopsy proven alcoholic cirrhosis of the liver and were followed up to a minimum period of two years after study: six died within this period. Ten alcoholic non-cirrhotic subjects (4 women and 6 men; age 45±7 years) and, 20 healthy volunteers (6 women and 14 men; age 52±12 years) served as concurrent controls. Patients were classified in three groups according to their degree of liver insufficiency as assessed by the Orrego index (Orrego et al, Gastroenterology 76:105 (1979)).

Study Protocol:

Blood was drawn on admission for the following measurements: (1) blood glucose and urea nitrogen, sodium, potassium, chloride, total calcium, phosphate, magnesium, creatinine, uric acid, total cholesterol, triglycerides, LDL-cholesterol, HDL-cholesterol, serum aspartate and alanine aminotransferases, gamma-glutamyl transpeptidase, 5'-nucleotidase, alkaline phosphatase, serum protein electrophoresis, complete blood count, prothrombin time, activated partial thromboplastin time, fibrinogen and alphafetoprotein; (2) serum 1gG, 1gA and 1gM, determined by radial immunodiffusion (Behring Diagnostics, Madrid); (3) serum C4, determined by hemolytic titration (Gaither et al, J. Immunol. 113:574 (1974)), and serum C3 and C3a desArg, determined by radial immunodiffusion (Behring Diagnostics); (4) plasma levels of zinc, measured by absorption spectrophotometry (pye Unicam SP 190); (5) circulating immune complexes, determined by [$^{12}$I]Clq binding (Zubler and Lamber In: Bloom and David, eds. In vitro Methods in Cell-Mediated and Tumor Immunity, New York: Academic Press pp 565–72(1976)); (6) peripheral-smear examination after Wright-Giemsa staining to assess the presence of Howell-Jolly bodies as an index of splenic function (Boyko et al, Am. J. Clin. Pathol. 77:745 (1982)) (negative in all patients); (7) macrophage Fcγ-receptor-dependent clearance in vivo; and (8) Fcγ-receptor-mediated recognition of sensitized cells by peripheral-blood monocytes in vitro; and (9) abdominal ultrasound to assess for the presence of splenomegaly, which was detected in 17 out of the 49 patients.

Preparation of human IgG anti-Rh(D):

Human IgG anti-RH(D) was prepared from serum from a single donor (was HIV-1 negative by ELISA-Pasteur Institute, Madrid-, Western Blott-Pasteur Institute, Madrid- and the quantitative end-point dilution method) by ammonium sulfate preciptation followed by Sephacryl S-300 gel filtration and QAE ion-exchange chromatography (Pharmacia, Madrid). No IgM was detected by double immunodiffusion (Ouchterlony analysis). The final IgG fraction was passed through a Millipore filter and tested for pyrogenicity and sterility. The final IgG fraction was HIV-1 negative by ELISA (Pasteur Institute, Madrid), Western Blott (Pasteur Institute, Madrid) and the quantitative end-point dilution method (Ho et al, N. Engl. J. Med. 321:1621 (1989)).

Macrophage Fcγ-receptor-mediated clearance:

Clearance studies were performed as previously described (Ruiz et al, N. Eng. J. Med. 322:717 (1990); Frank et al, N. Engl. J. Med. 300:518 (1979); Schreiber and Frank, J. Clin. Invest. 51:575 (1972)). In brief, erythrocytes (RhD) were isolated from all subjects, washed three times in physiologic saline, spectrophotometrically standardized to a concentration of 6.6×10 cells per milliliter, and radiolabeled with $^{51}$Cr (potassium dichromate, Amersham, Buckinghamshire, England). An aliquot of cells was sensitized by adding to it drop by drop an appropriate dilution of the purified human IgG anti-Rh(D). The mixture was incubated at 37° C. for 30 minutes, and the sensitized $^{51}$Cr-labeled erythrocytes were washed four times in saline and resuspended to a concentration of 3.3×10 per milliliter in Hanks' balanced salt solution (M.A. Bioproducts, Madrid). An aliquot of cells (usually 10 ml, with 2.5 µCi of radioactivity) was injected through an antecubital vein, and the survival of red cells was determined in serial blood samples obtained over a period of 48 hours. Clearance curves were plotted by expressing the number of counts per minute at each time point as a percentage of the number of counts at 10 minutes, the zero point. The time required for clearance of the 50 percent of the inoculated IgG-coated red cells (half-time) was calculated and then correlated with clinical and serologic data. In addition, for the clearance on each day, the percentage for the inhibition of clearance above control was calculated at 1, 1.5, 2, 8, 24 and 48 hours, according to the formula $$\% \text{ inhibition} = 100 \times 1 - \frac{(CPMb - CPMx)}{(CPMb - CPMc)},$$

where CPMb denotes the number of counts per minute in a control subject who received an injection of unsensitized autologous red cells, CPMx the number of counts in a patient who received IgG-coated (sensitized) autologous red cells, and CPMc the number of counts in a control subject who received autologous IgG-sensitized red cells. By means of this formula, patients could be compared with controls studied on the same day, and results could be expressed as the percentage of change in clearance, where 100 percent inhibition of clearance indicated that clearance in a patient who received IgG-coated red cells (CPMx) was identical to clearance in a control who received unsensitized red cells (CPMb) (Friedman, J. Clin. Invest. 75:162 (1985)). In three additional control groups—five patients with alcoholic cirrhosis of the liver, five noncirrhotic alcoholic subjects, and five healthy volunteers—the clearance of autologous $^{51}$Cr-labeled but unsensitized red cells and the clearance of $^{51}$Cr-labeled heat-damaged autologous red cells were examined.

Duplicate studes were performed in nine of the patients with alcoholic cirrhosis of the liver in whom severe infection had developed, six of the patients with alcoholic cirrhosis of the liver without a history of complications due to infection, and six controls. The results of the repeat studies of clearance were unchanged from those of the original studies in each subject. Serum C3, C3a desArg, and C4 were measured to assess complement activation during the clearance of IgG-coated red cells. No significant complement activation was observed in any of the patients included in the present study.

Number of IgG (Anti-RhD) molecules per red cell:

The number of IgG molecules per red cell was determined as previously described with the use of $^{12}$-labeled anti-IgG reagent (Cines and Schreiber, N. Engl. J. Med. 300:106 (1979)). Clearance studies were always performed with erythrocytes sensitized so that approximately 600 molecules of IgG were present on each red cell. When Fcγ-receptor-dependent recognition by blood monocytes was studied in vitro, each red cell (RhD) was coated with 400, 800, or 1600 molecules of 1gG.

Binding of IgG(Anti-RhD)-coated red cells:

The recognition of 1gG-coated red cells (RhD) by monocytes isolated was determined as previously described (Gomez et al, J. Reticuloendothel. Soc. 31:24 (1982); Schreiber et al, J. Clin. Invest. 56:1189 (1975)). In brief, confluent monolayers of 5.5×10 monocytes were obtained from defibrinated blood after density-gradient centrifugation (Ficoll-Isopaque) and plastic adherence to petri dishes (Nunc, Amsterdam). An aliquot of 2×10$^7$ $^{51}$Cr-labeled, IgG-coated red cells (RhD) was added to each monocyte monolayer. The petri dishes were then incubated at 37° C. in an atmosphere of 5 percent carbon dioxide for 45 minutes, washed to detach unbound red cells, and treated with 0.086 M EDTA solution to remove adherent monocytes and monocyte-bound IgG (Anti-RhD)-sensitized red cells. The treatment with EDTA removed all adherent monocytes and all radioactivity. The percentage of $^{51}$Cr-labeled and IgG-sensitied red cells (RhD) recognized by peripheral-blood monocytes was determined according to the formula:

$$\% \text{ red-cell IgG bound to monocyte monolayers} = \frac{\text{cpm for IgG (anti-RhD)-coated red cells removed with EDTA}}{\text{cpm for IgG (anti-RhD)-coated red cells added to monocyte monolayers}} \times 100.$$

No phagocytosis of anti-RhD-sensitized erythrocytes by peripheral blood monocytes occurs under the experimental conditions (Gomez et al, J. Reticuloendothel. Soc. 31:241 (1982); Schreiber et al, J. Clin. Invest. 56:1189 (1975)). The studies were repeated in 6 controls, 6 non-cirrhotic alcoholic patients, 9 of the patients in whom severe infection developed and 6 of the patients with no history of infectious complications; the results of the repeat studies were unchanged from those of the original studies in each subject.

Preparation of IgG2b-sensitized red cells:

Antibody-sensitized sheep erythrocytes (EA) were prepared as previously described (Rossman et al, Exper. Hematol. 21:177 (1993)). In brief, 1×10 sheep red blood cells in 1.0 ml of 0.01 mol/L EDTA buffer were sensitized by adding mouse monoclonal antibody Sp2/HL, subclass IgG2b (Serotec Ltd., Bicester, Oxon), in 0.1 ml at 37° C. for 1 hour. The final antibody dilutions used to prepare these cells were between 1:10 and 1:80. The IgG-sensitized (coated) sheep red cells were washed twice and resuspended in HBSS to a final concentration of 1×10 cells/ml. In addition, a polyclonal 7S IgG rabbit anti-sheep red blood cell (Cordis Laboratories) was also used to prepare polyclonal IgG-coated red blood cells. The final antibody dilution used to prepare these cells was 1:1000.

Monocyte recognition of sheep IgG-sensitized red blood cells:

Monocyte in vitro recognition of IgG-sensitized red cells was assessed as previously reported (Rossman et al, Exper. Hematol. 21:177 (1993); Schreiber et al, N. Engl. J. Med. 316:503 (1987)). In brief, 1×10 IgG-coated red cells or control unsensitized red cells were added to monocyte monolayers containing 1×10 cells. These cells were incubated at 4° C. or 37° C. in phosphate buffer at an ionic strength of $\mu=0.07$ or $\mu=0.15$, respectively. After 2 hours, the plates were washed and stained with Wright's Giemsa. Two hundred (200) monocytes were counted under light microscopy in a blinded fashion to assess the number of IgG-sensitized red blood cells bound per monocyte. Monocytes binding >3 red blood cells/monocyte were determined. These experiments were performed in 5 patients of each alcoholic cirrhosis of the liver groups (I, II and, III), 5 alcoholic non-cirrhotic subjects and 5 normal volunteers. The experiments were repeated in these same patients and controls at least one year after the initial studies. No significant variations were found between the initial experiments and the ones performed after more than one year.

HLA typing:

HLA typing was performed by the tissue-typing laboratory of the Virgen del Rocio University Hospital, Seville, Spain.

Assessment of nutritional status:

Nutritional status was evaluated according to anthropometric, biochemical, and immunologic measurements (Blumonkrantz et al, Am. J. Clin. Nutr. 33:1567 (1989); Harvey et al, Am. J. Clin. Nutr. 33:1587 (1989); Feliffe, Wo 1966, No. 53, Geneva, Switzerland; Bristian et al, JAMA 235:1567 (1976)). Dry body weight, relative body weight, and the percent ideal body weight were also determined. The anthropometric data were compared with standard values for the local population (Jaurrieta, Med. Clin. 81:584 (1983)). Serum albumin and transferrin were measured to evaluate the serum protein level. Malnutrition was classified according to previously established criteria (Blumenkrantz et al, Am. J. Clin. Nutr. 33:1567 (1980); Harvey et al, Am. J. Clin. Nutr. 33:1586 (1980); Feliffe, WO 1966 No. 53, Geneva, Switzerland; Bristian et al, JAMA 235:1567 (1976); Jaurrieta, Med. Clin. 81:584 (1983); O'Keefe et al, Lancet 2:615 (1980)) as marasmus, kwashiorkor, or mixed type. All malnourished patients had malnutrition of the mixed type. A high incidence of protein-calorie malnutrition of the mixed type was observed in 17 of the 49 patients (35 percent). Total body weight did not change. Cutaneous hypersensitivity responses to standard concentrations of four antigens-purified protein derivative, Trycophyton rubrum, Candida albicans, and streptokinase-streptodornase were used to evaluate cell-mediated immunity as previously described (Harvey et al, Am. J. Clin. Nutr. 33:1586 (1980); Blackburn et al, J. Parenter. Enteral. Nutr. 1:11 (1977)). A response was considered positive when the diameter of induration was more than 5 mm. A normal response was indicated by a positive response to either three or four antigens, an abnormally low response by a positive response to either one or two antigens, and anergy by a lack of positive response to any of the four antigens.

Statistical analyses:

The in vivo clearance curves were analyzed at the time points to calculate a P value for the difference between the controls and patients by Student's t-test. The in vitro Fcγ-receptor-dependent recognition of red cells by monocytes and the clearances in patients and controls were assessed with the Wilcoxon rank-sum test for unpaired data. The relation of the clearance rate (as half-time) or monocyte Fcγ-receptor-dependent recognition of IgG-coated red cells in vitro to the seologic tests was analyzed with the Spearman rank-correlation test.

Figure 4:
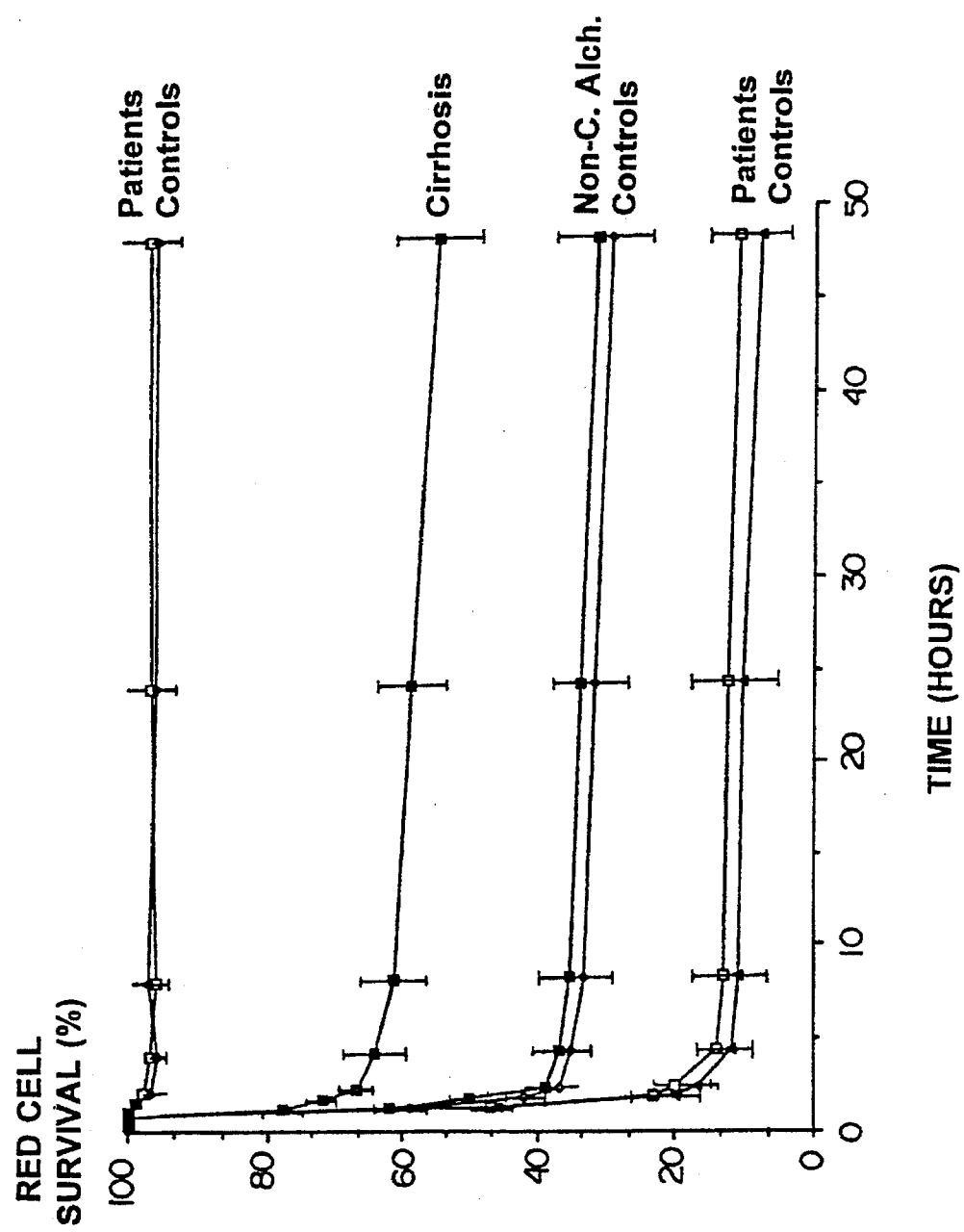
FIG. 4—Macrophage Fcγ-receptor-mediated clearance of IgG-sensitized radiolabeled red cells in patients with alcoholic cirrhosis of the liver (n=49), non-cirrhotic alcoholic subjects (n=10) and healthy volunteers. The middle three curves (means±SEM) represent values for clearance of IgG-sensitized red cells in these 79 subjects; the upper pair of curves, the clearance of unsensitized autologous red cells in five patients and five controls; and the lower pair of curves, the clearance of heat-damaged red cells (heated for 30 minutes at 56° C.) in five patients and five controls.

Clearance Study Results:

Clearance studies were performed in the 49 patients with alcoholic cirrhosis of the liver fulfilling the inclusion criteria of this study. The results demonstrated that the clearance of IgG-coated red cells was significantly impaired (p<0.001) (FIG. 4). At 1 and 1.5 hours, the mean (±SEM) inhibition of macrophage Fcγ-receptor-mediated clearance was 47±3 and, 53±3 percent, respectively. Clearance was inhibited by more than 15 percent in 37 patients and, by 5 to 12 percent in 6. In contrast, the clearance of unsensitized red cells and of heat-damaged red cells in the patients did not differ from the clearance of these cells in the non-cirrhotic alcoholics and healthy volunteers (FIG. 4).

Figure 5:
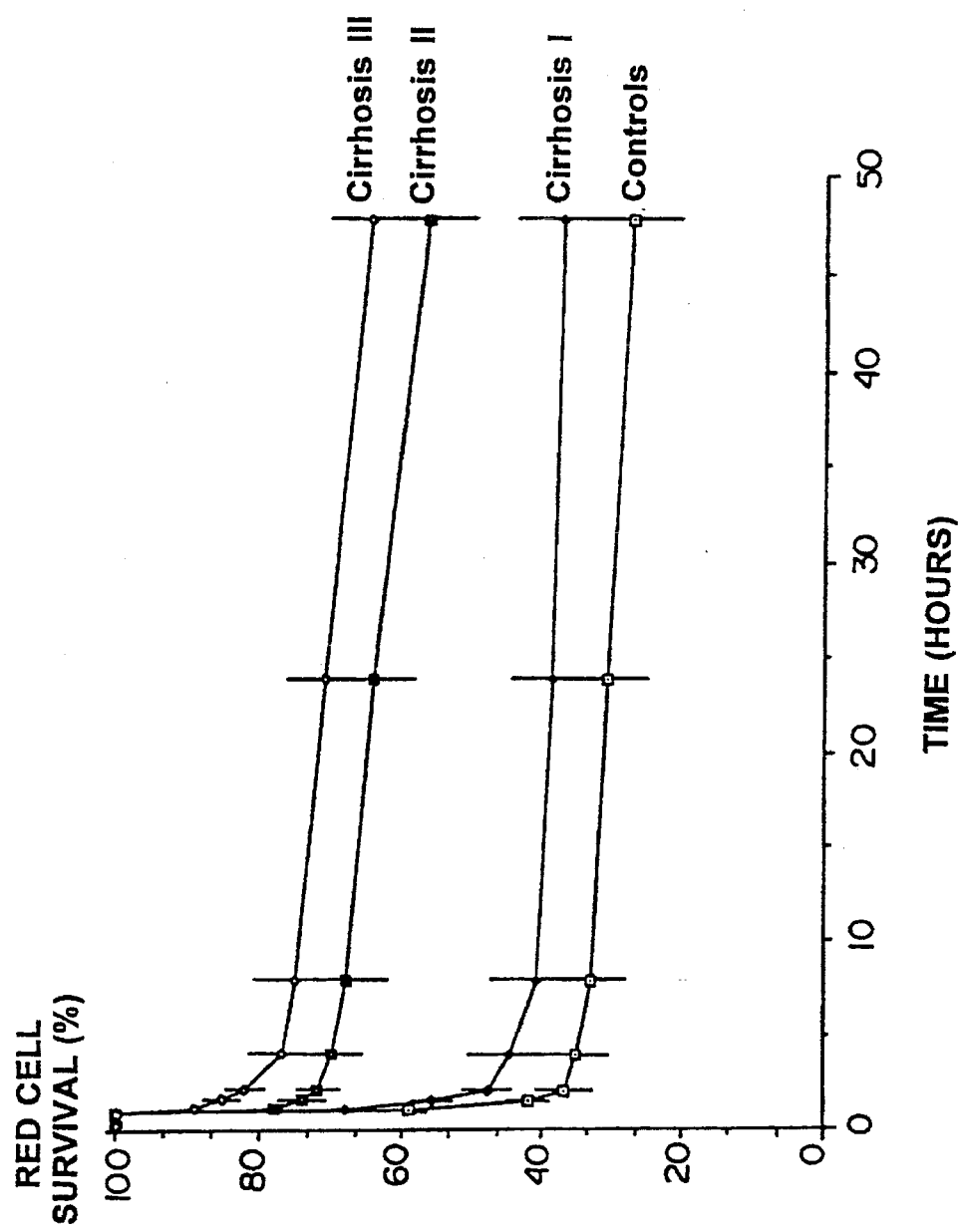
FIG. 5—Macrophage Fcγ-receptor-mediated clearance of IgG-sensitized radiolabeled red cells in patients with alcoholic cirrhosis of the liver (n=49), and healthy volunteers (n=20). The four middle curves (means±SEM) represent values for clearance in these 69 subjects: patients with mildly decompensated alcoholic cirrhosis of the liver (cirrhosis I, n=17), patients with moderately decompensated alcoholic cirrhosis of the liver (cirrhosis II, n=17), patients with severely decompensated alcoholic cirrhosis of the liver (patients III, n=15), and controls (n=20).

Patients were classified in three groups according to their degree of liver insufficiency as assessed by the Orrego index. Clearance studies of those three groups of patients are represented in FIG. 5. The results demonstrated that the clearance of IgG-coated red cells was significantly impaired (p<0.001) in patients with moderate (Patients II or group II) and severe (Patients III or group III) liver insufficiency. At 1 and 1.5 hours, the mean (±SEM) inhibition of macrophage Fcγ-receptor-mediated clearance was 47±3 percent and 66±4 percent, respectively, for group II patients. At 1 and 1.5 hours the mean (±SEM) inhibition of macrophage Fcγ-receptor-mediated clearance of 1gG-coated red cells was impaired in patients with mild liver insufficiency (Patients I or group I), (FIG. 5), but the difference was not significant.

Figure 6:
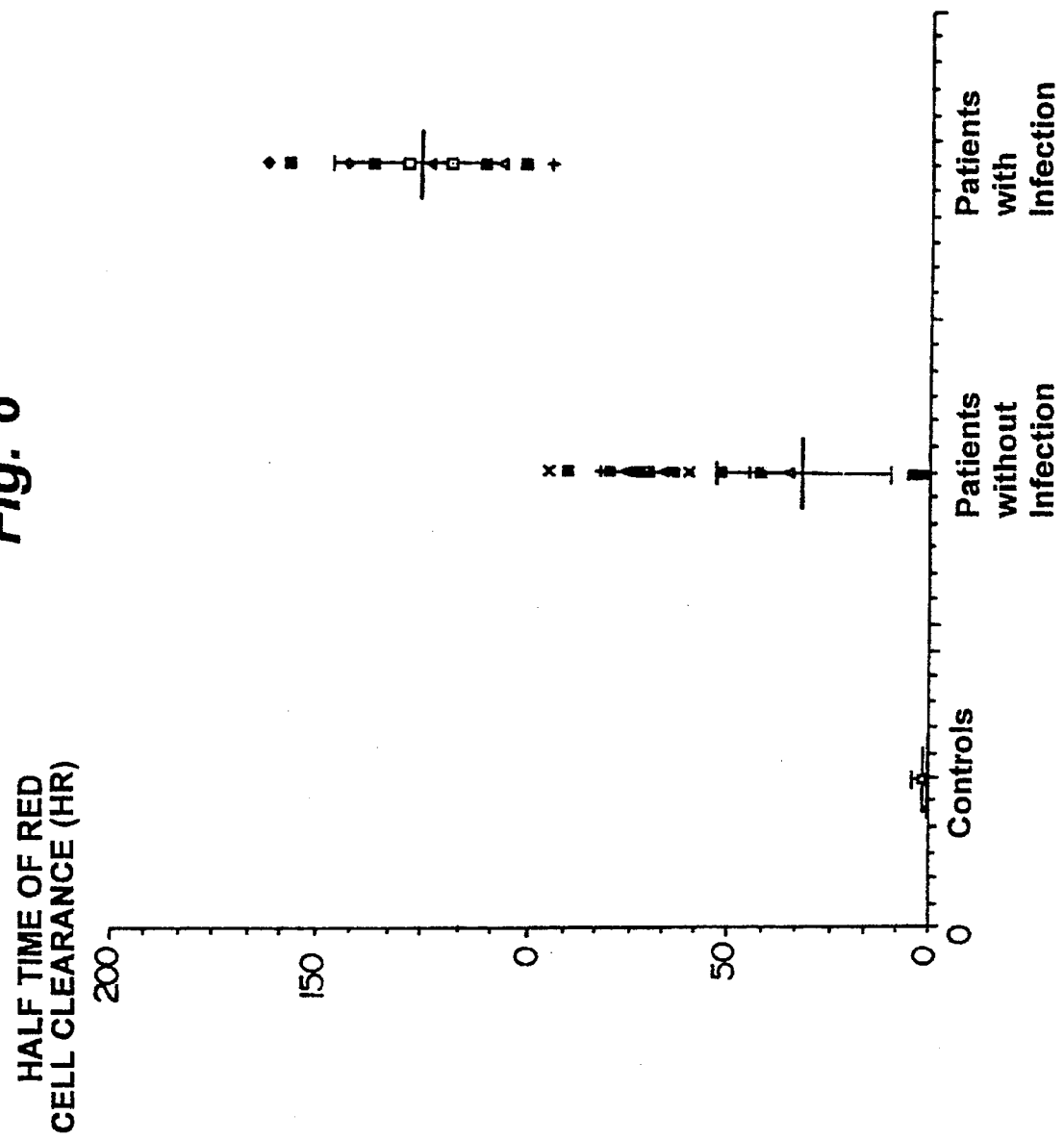
FIG. 6—Macrophage Fcγ-receptor-mediated clearance of IgG-coated red cells (as half-time) in patients with alcoholic cirrhosis of the liver (n=49) and in controls (n=20). The half-time was significantly longer in the eleven patients in whom severe infection developed during follow-up.

The patients were followed up for at least two years after the clearance studies were initially performed. Six patients died, two of massive hemorrhage from ruptured esophageal/gastric varices (15th and 17th month of follow up, respectively), two spontaneous bacterial peritonitis by E. coli (14th and 20th month of follow up, respectively), and two Gram-negative sepsis due to E. coli and (16th and 21st month of follow up, respectively). Eleven patients had severe infection: five had spontaneous bacterial peritonitis (*E. coli*) and, six had sepsis (due to *E. coli* in three, *Staphyloccus aureus* in one, in one, and *Serratia marcescens* in one). When the clearance of IgG-coated red cells in the patients with severe infection was compared with the clearance in the patients without infection, those with infection were found to have a significantly longer half-time (126.2±22 vs. 32.2±18 hours; $p<0.001$)(FIG. 6). The clearance of IgG-coated red cells was analyzed in the patients (half-time) in relation to various parameters of liver impairment (SGOT, SGPT, GGT, 5'-nucleotidase, bilirubin -total, direct and indirect-, P.T., aPTT, fibrinogen and serum albumin). None of these parameters, including the presence of splenomegaly, correlated with the extent of impairment of clearance of IgG-coated red cells.

Figure 7:
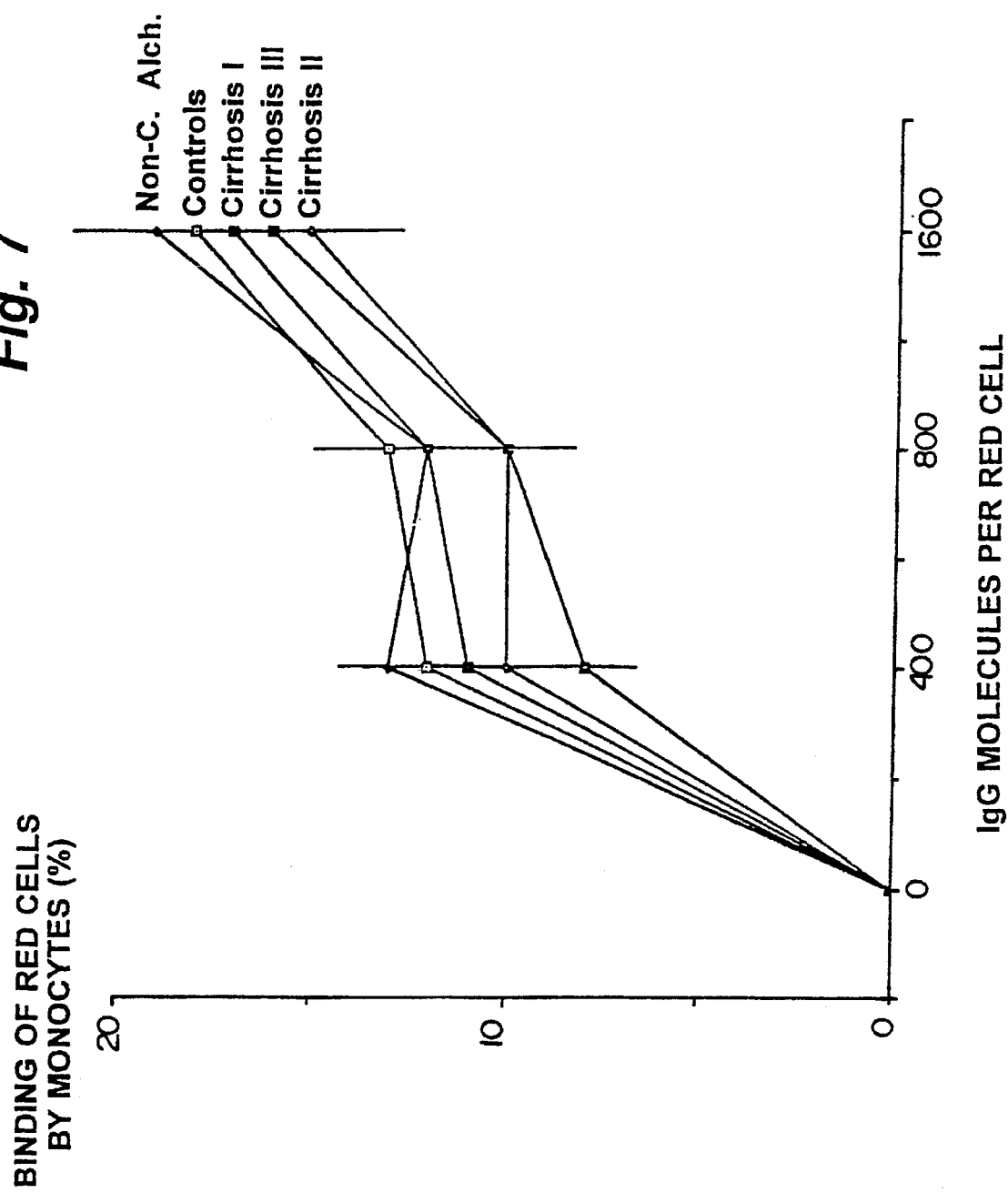
FIG. 7—Recognition of human IgG(anti-RhD)-coated red cells by monocytes from patients (n=49) and controls (n=20). IgG-sensitized, $^{51}Cr$-labeled $(2\times10)^7$ erythrocytes were added to monolayers of monocytes, and the percentage of red cells bound by monocytes was determined by measuring the radioactivity. Values are means ±SEM.

Isolated peripheral blood monocytes were also studied (FIG. 7). Erythrocytes from a single Rh(D)-positive donor were sensitized with three different concentrations of IgG-antiRh(D) (400, 800, and 1600 IgG molecules per red cell). Monocytes isolated from the patients bound fewer IgG-coated red cells than did those from the controls, but the difference was not significant. There was no correlation between the extent of binding by monocytes and the degree of impairment of clearance of IgG-coated red cells. No difference was observed between this alteration in monocyte FcγRI in patients in whom severe infection developed and those in whom it did not.

Figure 8:
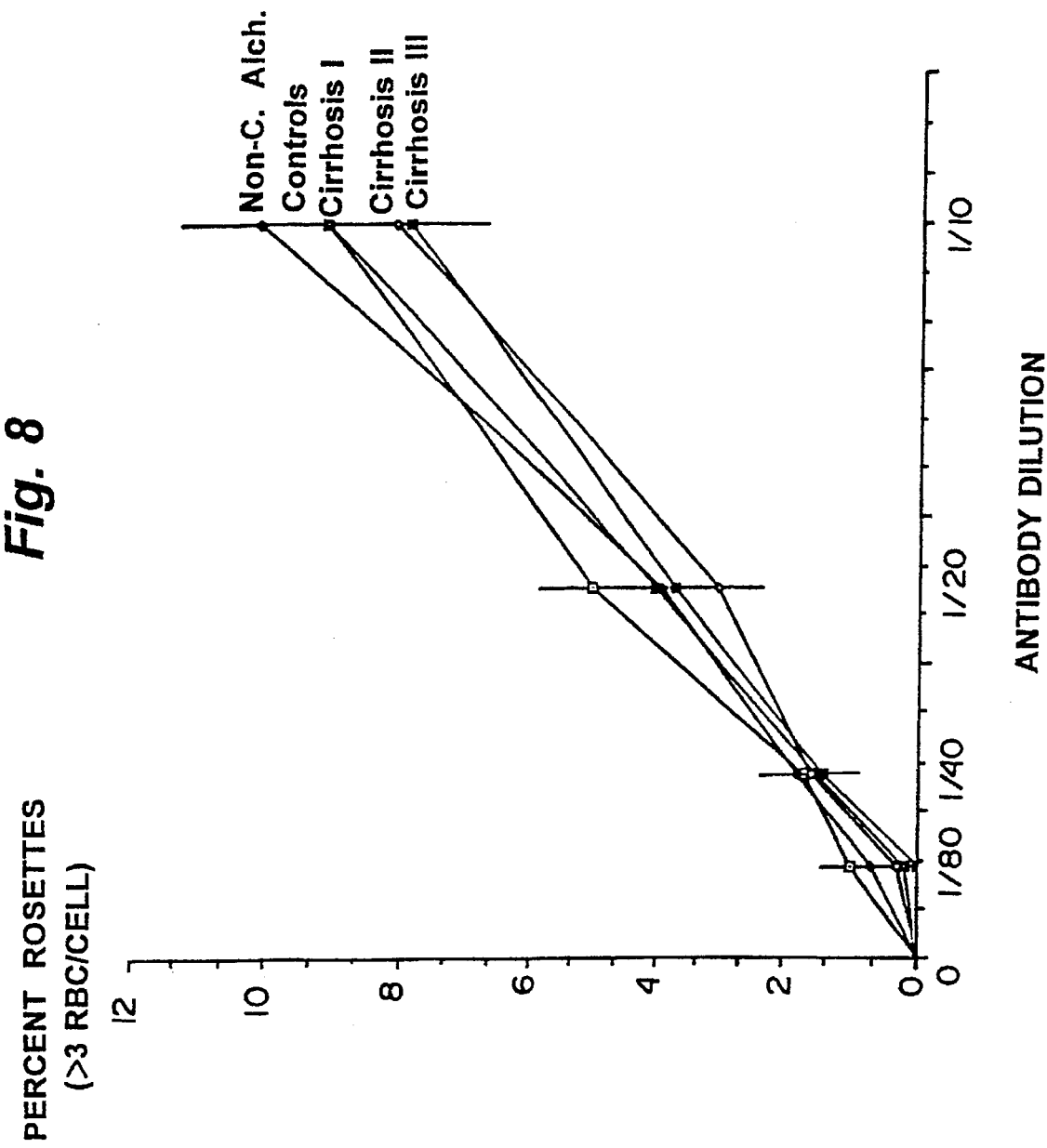
FIG. 8—Recognition of mouse IgG2b-coated red cells by monocytes from patients (n=49) and controls (n=20). IgG2b-sensitized erythrocytes were added to monolayers of monocytes, and the percentage of monocytes binding >3 RBC per cell was determined. Values are means ±SEM.

The function of monocyte FcγRII was assessed in vitro by the binding of IgG2b-coated red blood cells (FIG. 8). Peripheral blood monocytes isolated from patients with cirrhosis of the liver bound less IgG2b-sensitized red cells than monocytes from non-cirrhotic alcoholic subjects or monocytes from normal volunteers, but the difference was not significant.

Figure 9:
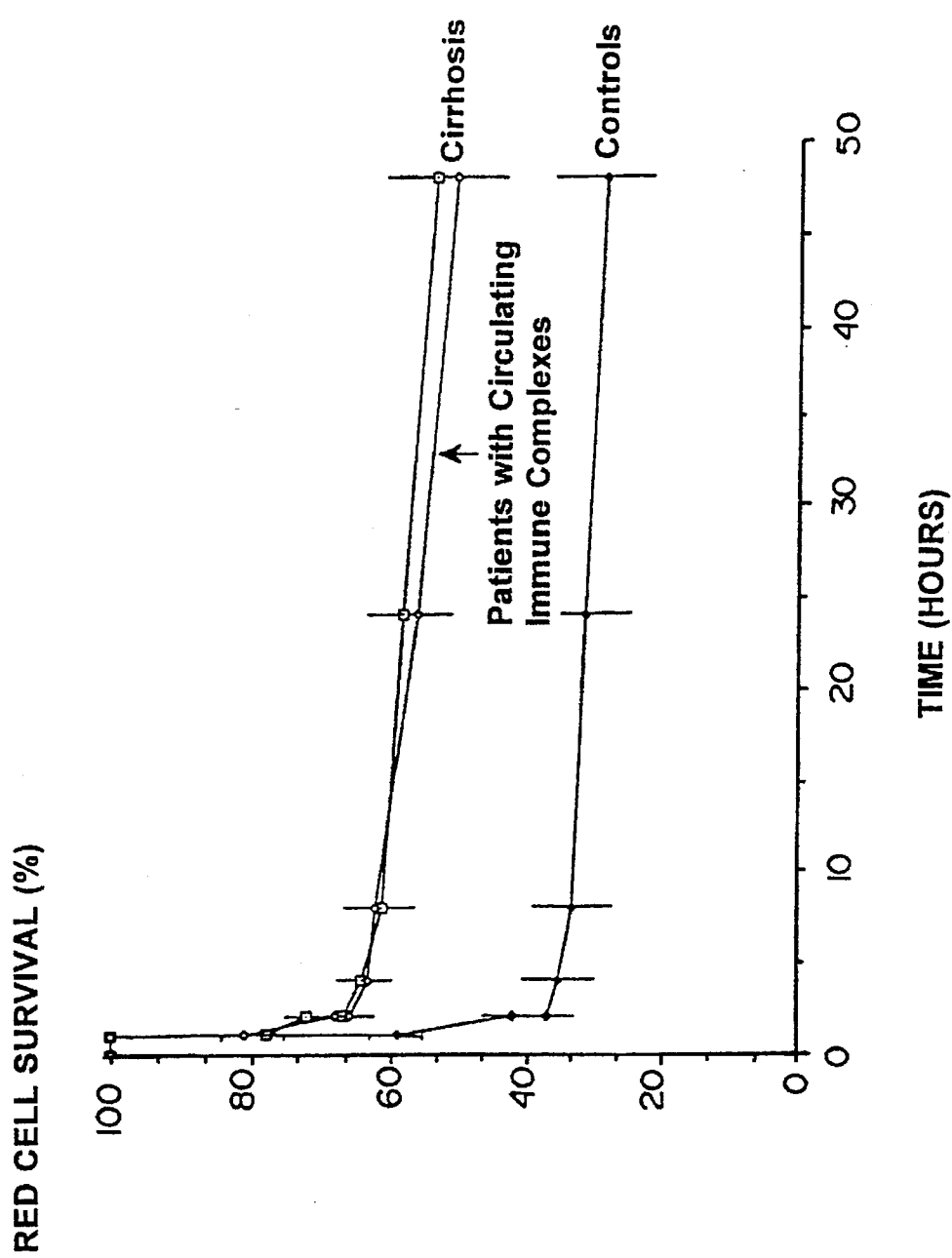
FIG. 9—Macrophage Fcγ-receptor-mediated clearance in patients with circulating immune complexes (n=7). The curves for these patients fell into the range for the patient group.

Seven patients had elevated levels of circulating immune complexes. The clearance of IgG-coated red cells in these patients did not differ from that observed in the patients in general (FIG. 9). Furthermore, there was no correlation in these five patients between the level of circulating immune complexes and the extent of impairment of the recognition of IgG-coated red cells by monocytes.

Neither the clearance of IgG-sensitized erythrocytes, nor the recognition in vitro of IgG-coated red cells or IgG2b-coated red cells by monocytes from the patients correlated with their sex, age, time from diagnosis of alcoholic cirrhosis of the liver or with any of the serologic measurements, including the immunoglobulin level. Furthermore, there was no relation between either the clearance of IgG-coated red cells or their recognition in vitro by monocytes and the HLA haplotype, or the nutritional status of the population studied.

The plasma zinc level was 18.4±0.7 μmol per liter (120 μg per deciliter) in healthy volunteers and 12.7±1.3 μmol per liter (83.3±3.7 μg per deciliter) in the patients with alcoholic cirrhosis of the liver ($p<0.001$). However, there was no correlation between the plasma zinc level and the degree of impairment of clearance in vivo or the monocyte recognition of IgG-coated red cells in vitro. Similarly, malnutrition was not necessarily linked with greater impairment of the clearance rate or a lower value for in vitro monocyte recognition of IgG-sensitized red cells. The prevalence of malnutrition was significantly higher in the patients with either moderate or severe liver insufficiency (groups II and II, respectively) ($p<0.001$). However, neither the macrophage Fcγ-receptor-mediated clearance nor the binding of IgG (Anti-RhD)-coated red cells or the binding of IgG2b-coated red cells by monocytes correlated with the nutritional status of these patients, as indicated by anthropometric, biochemical, and immunologic values.

EXAMPLE X

T-Cells Transfected with FcγRIIA

Experimental Protocols:

Cell lines and antibodies:

The Jurkat T-cell line J32 and the CD2-CD28-CD3+ variant J32-3.2 have been described previously (Makni et al, J. Immunol. 146:2522 (1991) and Sancho et al, J. Immunol. 150:3230 (1993)). These cell lines were maintained in RPMI 1640 containing 10% heat inactivated FCS (Hyclone Laboratories, Utah), 2 mM L-glutamine, penicillin (100 U/ml) and streptomycin (100 U/ml). The following antibodies were used in this study: anti-CD2 mAbs 9.6 (Sancho et al, J. Immunol. 150:3230 (1993)) and 9.1 (Yang et al J. Immunol. 137:1097 (1986)), anti-CD3 mAb 64.1 (Hansen et al, In Leukocyte Typing, Bernard et al eds. Springer-Verlag, New York p. 195 (1984)) and anti-FcγRII mAb IV.3 (Fanger et al, Immunol. Today 10:92 (1989)).

Construction of the FcγRIIA expression vector and DNA transfer into J32 and J32-3.2 cell lines:

FcγRIIA cDNA was isolated from the plasmid pKC4 (Hibbs et al, Proc. Natl. Acad. Sci. USA 5:2240 (1988)) using EcoR1 and the fragment was blunt ended using Klenow polymerase. The FcγRIIA cDNA was then inserted into the Sma1 site of plasmid pGSE1731 (Greaves et al, Cell 56:979 (1989)) under control of the human β-globin gene promoter and enhancer sequences. pGSE1731 contains 4.9 Kb of the human β-globin gene including 1.5 Kb of sequences upstream of the CAP site and the internal and 3' enhancer regions. This plasmid also contains the CD2 3' enhancer region which confers T-cell specific, position-independent gene expression (Greaves et al, Cell 56:979 (1989)). The resulting plasmid, pGSE2A was introduced into the J32 and J32-3.2 cell lines by electroporation using methods previously described in detail (Sancho et al J. Immunol. 150:3230 (1993)). Prior to electroporation, pGSE2A was linearized by digestion with NotI. Each electroporation was carried out using 30 μg of linearized pGSE2A and 5 μg of pcEXV Neo linearized with EcoRI. After electroporation, the cells were cultured for seven days in the presence of 0.3 mg/ml G418 and assayed for FcγRIIA expression by flow cytometry. FcγRIIA expressing cells were enriched by immunomagnetic positive selection using magnetic particles coated with IgG (Dynal Inc., Fort Lee, N.J.). Cells were cultured in flat buttomed microtitre wells (approx. 100 cells per well) and clones were selected and analyzed for FcγRIIA expression by flow cytometry.

Tyrosine Phosphorylation Results:

Stimulation of the T-cell receptor (TCR)/CD3 complex in Jurkat T-cells induces the tyrosine phosphorylation of proteins including the TCR-associated ζ chain, the ZAP70 tyrosine kinase and the CD3ε complex (Weiss, Cell 79:209 (1993)). Similarly, in the members of the IgG family of receptors, induction of tyrosine phosphorylation accompanies receptor activation (Samelson and Klausner, J. Biol. Chem. 267:24913 (1992)) and, accordingly, studies were conducted to determine if stimulation of FcγRIIA in the T-cell transfectants J32/FcγRIIA and J32-3.2/FcγRIIA induced tyrosine phosphorylation. The mutant J32-3.2 cell line is deficient in the induction of tyrosine phosphorylation signalling pathways leading to impaired induction of phosphorylated ZAP70, ζ chain and CD3ε after TCR crosslinking (Sancho et al, J. Immunol. 150:3230 (1993)). The activation of the Src-related tyrosine kinase (SRTKs) p56lck and p59fyn is also defective in this mutant (Sancho et al. J. Immunol. 150:3230 (1993)).

Figure 10:
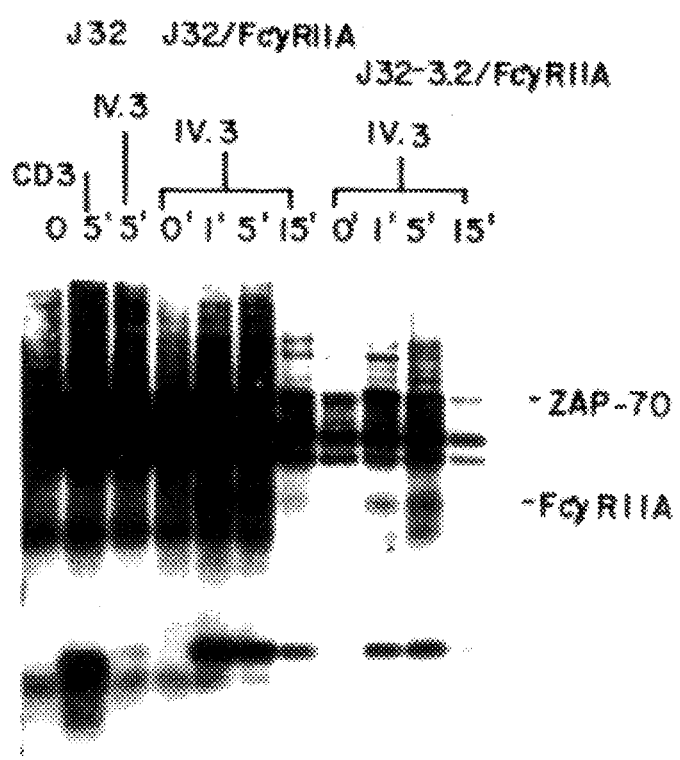
FIG. 10—Tyrosine phosphorylation in wild type J32 and in mutant J32-3.2 transfectants. Antiphosphotyrosine immunoblots were prepared following immunoprecipitation of cell lysates with either anti-phosphotyrosine antibody or anti-FcγRII antibody. The 40 kD FcγRII receptor is phosphorylated on tyrosine following FcγRII activation.

Stimulation of FcγRIIA by crosslinking with anti-FcγRII antibody followed by immunoprecipitation with antiphosphotyrosine antibody (Huange et al, J. Biol. Chem. 267:5467 (1992)), showed that the 40 kD FcγRII receptor is phosphorylated on tyrosines in both wild-type J32 and in the mutant J32-3.2 transfectants (FIG. 10, lanes 4–11 (the position of the 40 kD receptor is indicated with an arrow).

Figure 11A:
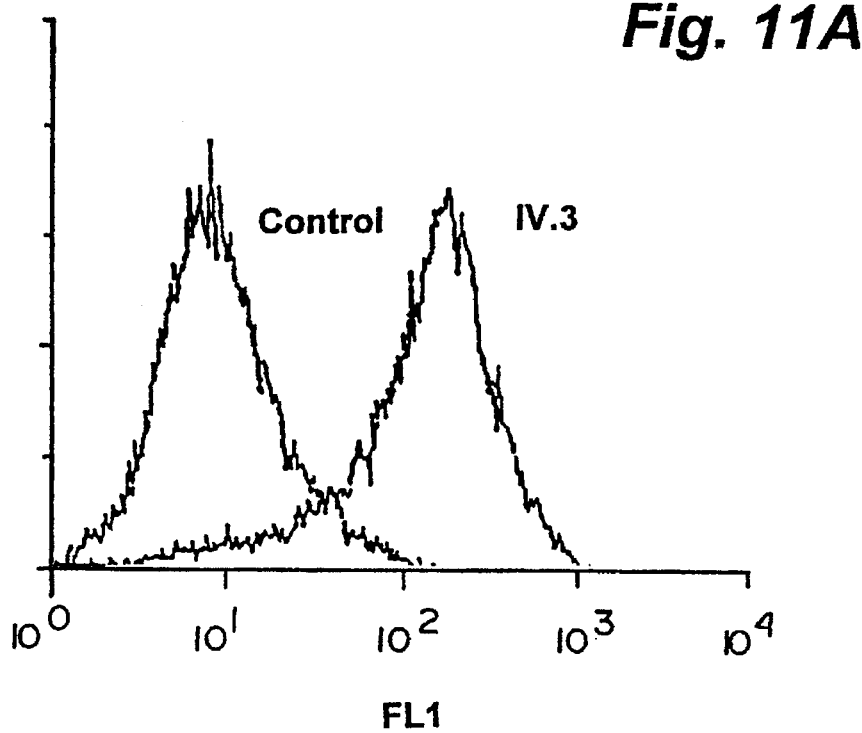
FIGS. 11A and 11B—Fluorescence histograms of J32/FcγRIIA and J32-3.2/FcγRIIA stable transfectants, and FcγRIIA expressing clones. Flow cytometry was employed with anti-FcγRII monoclonal antibody IV.3 or with an isotype control (Indik et al, J. Clin. Invest. 88:1766 (1991)).
Figure 11B:
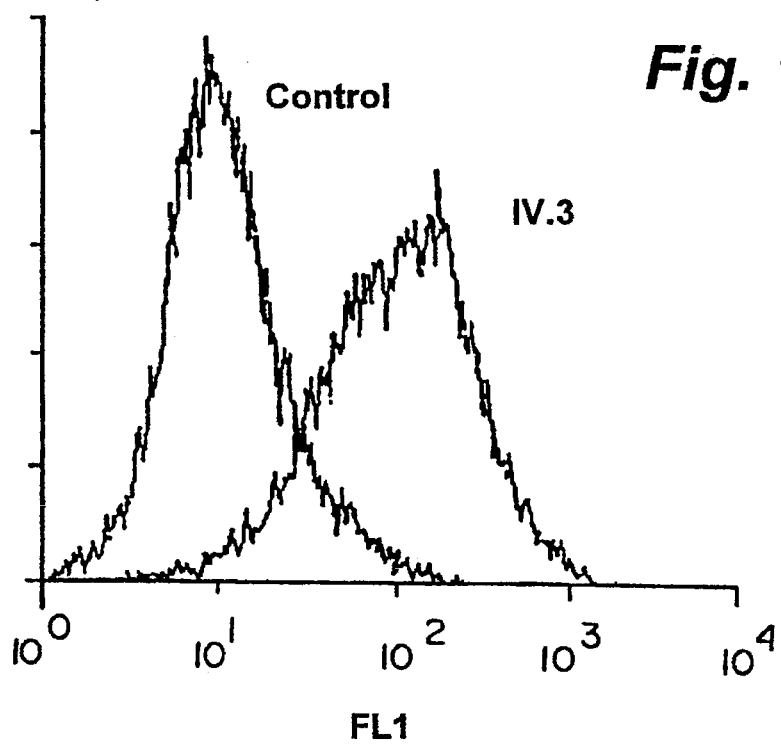

Phagocytosis Results:

FcγRIIA cDNA was expressed in the wild type Jurkat T-cell line J32 and in the mutagenized J32 variant, J32-3.2. As noted above, the J32-3.2 cell line is CD2-CD28-CD3+ and exhibits reduced signal transduction capabilities after TCR/CD3 stimulation, with respect to tyrosine phosphorylation pathways and GTP binding mechanism (Sancho et al, J. Immunol. 150:3230 (1993)). Calcium mobilization and IL2 promoter activity induced after TCR stimulation are also impaired (Sancho et al, J. Immunol. 150:3230 (1993)). Fluorescence histograms of J32/FcγRIIA and J32-3.2/FcγRIIA stable transfectants, and FcγRIIA expressing clones isolated from these transfected cells, are shown in FIGS. 11A and 11B.

Figure 12A:
FIGS. 12A and 12B—Phagocytosis of IgG coated erythrocytes by J32 and J32-3.2 transfectants. EA was prepared as described previously (Indik et al, J. Clin. Invest. 88:1766 (1991)), overlaid onto transfected or sham-transfected T-cells and incubated at 37° C. for 30 minutes. Unbound EA was removed by washing with PBS and extracellular bound EA was removed by exposure to hypotonic buffer before staining with Wright-Geimsa.
Figure 12B:
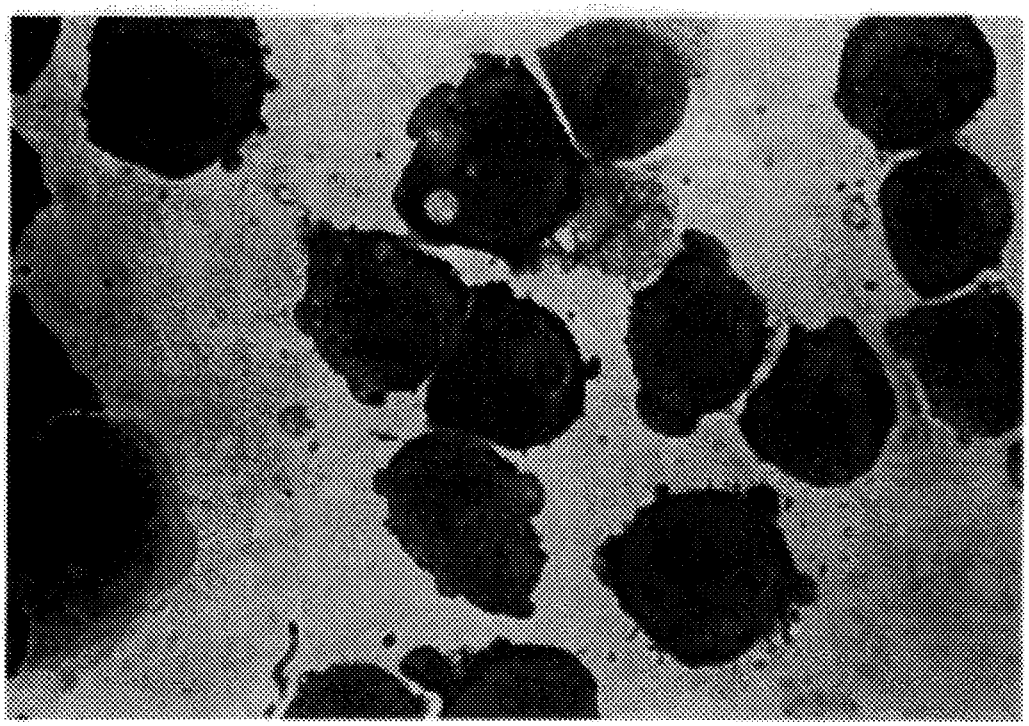

The ability of these T-cell transfectants to phagocytose IgG-sensitized cells was assessed by incubation with IgG coated sheep erythrocytes (sEA). In both the wild type J32 and mutant J32-3.2 transfectants, a number of the cells were able to phagocytose the sEA (FIGS. 12A and 12B). The results of several experiments with (a) bulk cell stable FcγRIIA-transfectants and (b) FcγRIIA clones are shown in Table 1. The data indicate that these T-cell transfectants phagocytose EA and that phagocytosis by the J32-3.2 mutant transfectants was reduced compared to the wild type cells.

TABLE 1

Phacocytosis of Sheep EA by FcγRIIA bulk cell stable transfectants of J32 and J32-3.2 cell lines.

|   | J32/FcγRIIA | | J32-3.2/FcγRIIA | | |
|---|---|---|---|---|---|
|   | % | P1 | % | P1 | cP1 |
| 1. | 17 | 28 | — | — | — |
| 2. | 33 | 22 | 5 | 6 | 7 |
| 3. | 25 | 40 | 13 | 18 | 21 |
| 4. | 32 | 53 | 17 | 21 | 24 |
| 5. | 31 | 51 | — | — | — |
| 6. | 14 | 21 | 6 | 8 | 9 |

P1 is the phagocytic index, i.e., the number of erythrocytes ingested per 100 cells. The corrected P1 value (eR1) is included in the J32-3.2/ FcγRIIA column to take into account the lower MF1 value observed in these transfected cells compared to the J32/FcγRIIA transfected cells. %=% phagocytic cells.

Considering that 70%–100% of the cells are expressing FcγRIIA in these transfectants, and presumably are mediating phagocytosis through this receptor, the levels of phagocytosis observed are relatively low when compared, for example, to COS-1 fibroblasts transfected with FcγRIIA (Indik et al, J. Clin. Invest. 88:1766 (1991)). However, the ingestion of the erythrocytes appears to be mediated via a genuine phagocytic process as preincubation of the cells in 10 µg/ml cytochalasin-D, a compound which inhibits actin polymerization (a process that is necessary for phagocytosis) (Indik et al, J. Clin. Invest. 88:1766 (1991)), abolished phagocytosis in these cells. Also phagocytosis was inhibited when the transfectants were incubated with sEA at 0° C. instead of 37° C.

All documents cited hereinabove are incorporated in their entirety by reference.

While the invention has been described with respect to what is presently regarded as the most practical embodiments thereof, it will be understood by those of ordinary skill in the art that various alterations and modifications may be made which nevertheless remain within the scope of the invention as defined by the claims which follow.

What is claimed is:

1. An Fcγ receptor comprising extracellular, transmembrane and cytoplasmic domains or functional portions thereof, from at least two of human FcγRI, human FcγRIIA, the α chain of human FcγRIIIA, and the γ chain of human FcγRIIIA, wherein the transmembrane domain of said receptor is not that of the α chain of human FcγRIIIA and wherein said domains, or portions thereof, are such that said Fcγ receptor renders phagocytic a COS-1 cell comprising same.

2. The receptor according to claim 1 wherein said cytoplasmic domain is the cytoplasmic domain of FcγRIIA or the γ chain of FcγRIIIA.

3. The receptor according to claim 1 wherein said receptor comprises the extracellular domain of the α chain of FcγRIIIA, the transmembrane domain of the γ chain of FcγRIIIA or FcγRI, and the cytoplasmic domain of the γ chain of FcγRIIIA.

4. The receptor according to claim 1 wherein said receptor comprises the extracellular domain of FcγRIIA and the transmembrane and cytoplasmic domains of the γ chain of FcγRIIIA.

5. The receptor according to claim 1 wherein said receptor comprises, in a single cytoplasmic domain thereof, at least two copies of the sequence Y-X2-L, wherein X2 represents any two amino acids.

6. The receptor according to claim 5 wherein X2 represents the amino acids of a Y-X2-L sequence of the cytoplasmic domain of FcγRIIA or the γ chain of FcγRIIIA.

7. An Fcγ receptor comprising, in a single cytoplasmic domain thereof, at least one copy of the sequence Y-X2-L in addition to the corresponding naturally occurring cytoplasmic domain, wherein said naturally occurring cytoplasmic domain includes at least one Y-X2-L sequence, wherein X2 represents any two amino acids and wherein said Fcγ receptor renders phagocytic a COS-1 cell comprising same.

8. The receptor according to claim 7 wherein X2 of said at least one additional Y-X2-L sequence represents the amino acids of a Y-X2-L sequence of the cytoplasmic domain of FcγRIIA or the γ chain of FcγRIIIA.

9. The receptor according to claim 7 wherein one copy of the Y-X2-L sequence is present in addition to the corresponding naturally occurring cytoplasmic domain.

10. An Fcγ receptor comprising in a single cytoplasmic domain thereof, at least one duplication in the number of Y-X2-L sequences present in the corresponding naturally occurring cytoplasmic domain, wherein said naturally occurring cytoplasmic domain includes at least one Y-X2-L sequence and wherein X2 represents any two amino acids and wherein said Fcγ receptor renders phagocytic a COS-1 cell comprising same.

11. The receptor according to claim 10 wherein X2 represents the amino acids of a Y-X2-L sequence of the cytoplasmic domain of FcγRIIA or the γ chain of FcγRIIIA.

12. The receptor according to claim 10 wherein said naturally occurring cytoplasmic domain is the cytoplasmic domain of FcγRIIA, the γ chain of FcγRIIIA or FceRI, and wherein X2 represent the amino acids of the Y-X2-L sequence of the cytoplasmic domain of FcγRIIA or the γ chain of FcγRIIIA or FceRI.

* * * * *